(12) United States Patent
Murphy et al.

(10) Patent No.: US 9,724,234 B2
(45) Date of Patent: Aug. 8, 2017

(54) IMPLANTING OVERSIZED OBJECTS INTO SURGICAL BEDS

(71) Applicant: The Regents of the University of California, Oakland, CA (US)

(72) Inventors: Christopher J. Murphy, Davis, CA (US); Erik R. Wisner, Davis, CA (US); Mark Mannis, Carmichael, CA (US); John H. Doval, Sacramento, CA (US); Kaitlin Murphy, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 88 days.

(21) Appl. No.: 14/360,607

(22) PCT Filed: Nov. 21, 2012

(86) PCT No.: PCT/US2012/066361
§ 371 (c)(1),
(2) Date: May 23, 2014

(87) PCT Pub. No.: WO2013/081943
PCT Pub. Date: Jun. 6, 2013

(65) Prior Publication Data
US 2014/0330374 A1 Nov. 6, 2014

Related U.S. Application Data

(60) Provisional application No. 61/564,815, filed on Nov. 29, 2011.

(51) Int. Cl.
*A61F 9/007* (2006.01)
*A61F 2/14* (2006.01)

(52) U.S. Cl.
CPC .............. *A61F 9/007* (2013.01); *A61F 2/14* (2013.01); *A61F 2/142* (2013.01)

(58) Field of Classification Search
CPC ...... A61F 2/1664; A61F 2/1662; A61F 2/148; A61F 2/142; A61F 9/007
See application file for complete search history.

(56) References Cited

U.S. PATENT DOCUMENTS

| 4,466,705 A | 8/1984 | Michelson |
| 6,755,858 B1 | 6/2004 | White |

(Continued)

FOREIGN PATENT DOCUMENTS

WO 2013/081943 6/2013

OTHER PUBLICATIONS

WO patent application No. PCT/US2012/066361, International Search Report and Written Opinion mailed Mar. 29, 2013.

(Continued)

*Primary Examiner* — Thomas McEvoy
(74) *Attorney, Agent, or Firm* — Weaver Austin Villeneuve & Sampson LLP

(57) ABSTRACT

The present invention relates to a deformable object to be implanted into a surgical site (exemplified by but not limited to a cornea lenticule, e.g., that could be native corneal tissue or a synthetic or biosynthetic construct), surgical instrumentation for altering the curvature and arc length of the deformable object to be implanted (e.g. corneal lenticule), as well as methods for introduction of the deformable object into the specifically prepared wound bed and for introduction of the deformable object.

10 Claims, 26 Drawing Sheets

(56) References Cited

U.S. PATENT DOCUMENTS

| | | |
|---|---|---|
| 2002/0055753 A1 | 5/2002 | Silvestrini |
| 2002/0163212 A1* | 11/2002 | Py ........................ A45C 11/005 294/1.2 |
| 2004/0049268 A1 | 3/2004 | Noolandi et al. |
| 2006/0287721 A1 | 12/2006 | Myung et al. |

OTHER PUBLICATIONS

WO patent application No. PCT/US2012/066361, International Preliminary Report on Patentability mailed Jun. 12, 2014.

* cited by examiner

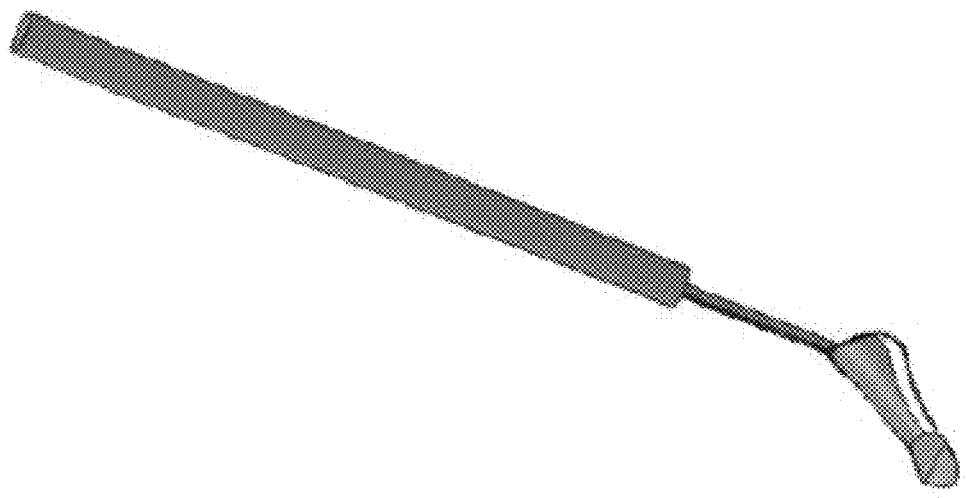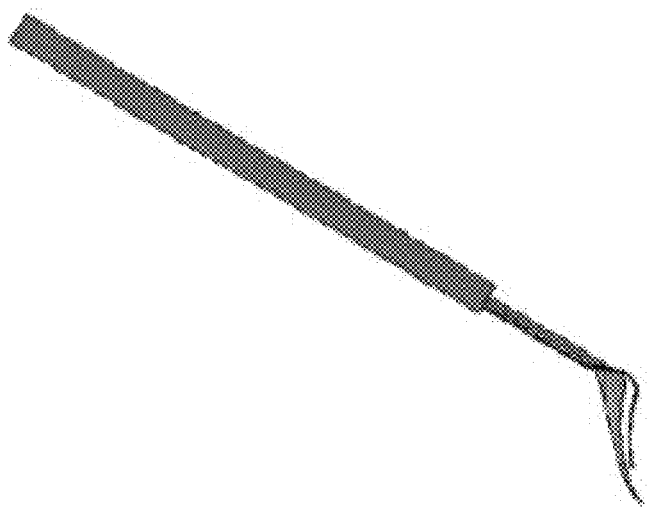
Fig. 7

A.

B.

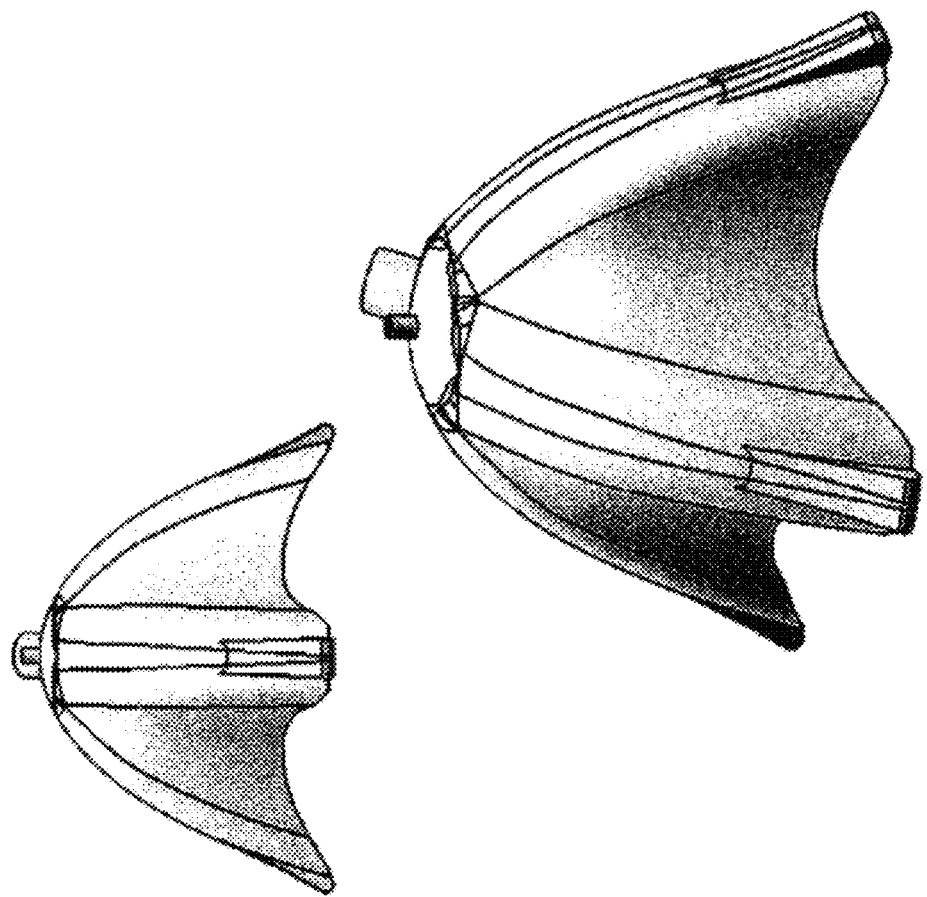
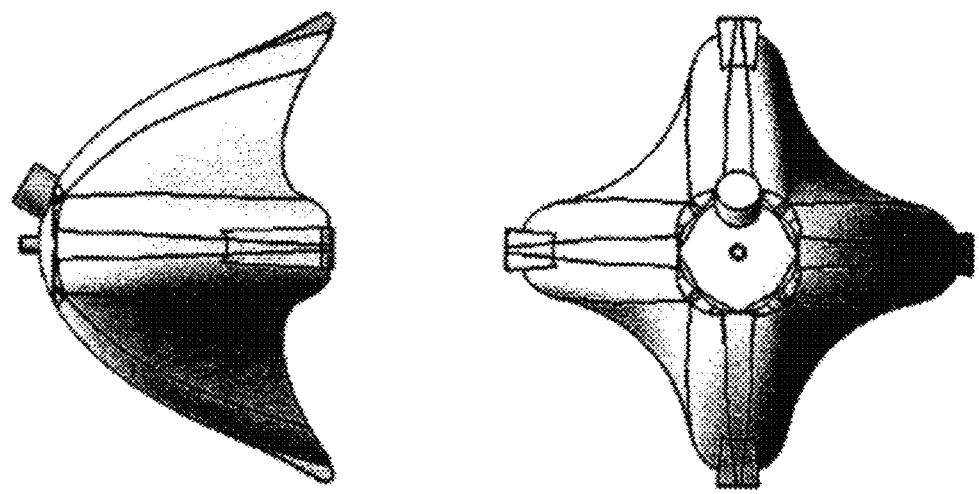
Fig. 14

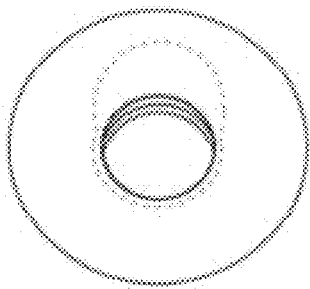

1. Corneal wound bed with dashed lines indicating location of asymetrical pocket extending outward from and on same stromal plane as encircling stromal pocket (dashed). The stromal pocket is located at mid-depth of the corneal stroma, extending outward.

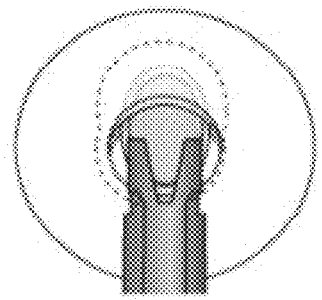

2. Corneal lenticule with thinner encircling "skirt", positioned in insertion device (used to decrease the radius and arc chord diameter of the lenticule) being inserted into asymetrically positioned stromal pocket. (Note that the "relaxed" full diameter of the lenticule exceeds the diameter of the superficial aspect of the corneal wound neccessitating use of the device to position it within the asymmetric pocket). Once advanced off the insertion device and into the stromal pocket, the corneal lenticule assumes it's "relaxed" full diameter.

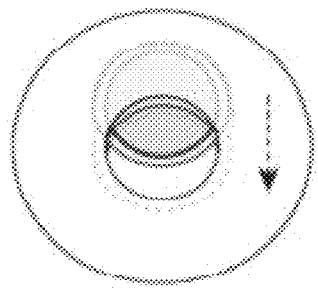

3. Lenticule in asymetrically positioned corneal stromal pocket. Once inserted and allowed to assume it's full relaxed diameter, it is subsequently repositioned (dashed arrow) such that the thicker central core is allowed to "pop" into and occupy the full thickness of the centrally located corneal wound bed.

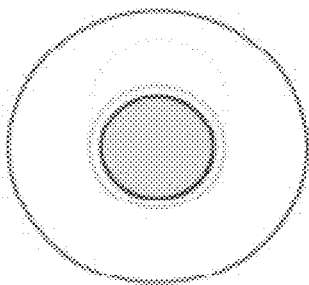

4. Centered lenticule in place. The peripheral skirt occupies the encircling stromal pocket.

*Fig. 17*

IMPLANTING OVERSIZED OBJECTS INTO SURGICAL BEDS

CROSS-REFERENCE TO RELATED APPLICATIONS

This application is a U.S. national phase under 35 U.S.C. §371 of International Application No. PCT/US2012/066361, filed on Nov. 21, 2012, which claims the benefit under 35 U.S.C. §119(e) of U.S. Provisional Application No. 61/564,815, filed on Nov. 29, 2011, which are hereby incorporated herein by reference in their entirety for all purposes.

FIELD

The present invention relates to a deformable object to be implanted into a surgical site (exemplified by but not limited to a cornea lenticule, e.g., that could be native corneal tissue or a synthetic or biosynthetic construct), surgical instrumentation for altering the curvature and arc length of the deformable object to be implanted (e.g. corneal lenticule), as well as methods for introduction of the deformable object into the specifically prepared wound bed and for introduction of the deformable object.

BACKGROUND

The deformable object is for implantation into a surgically prepared recipient bed. The diameter of the deformable object, in its full "relaxed" state would exceed the diameter of the superficial aspect of the surgical site with a surgical pocket being created deep to the superficial aspect of the surgical site that would accommodate the full relaxed diameter of the deformable object to be implanted. A deformable object is exemplified by but not limited to a corneal lenticule for implantation. In various embodiments, the lenticule is intended for use as a lamellar graft (not full thickness) or a full thickness penetrating keratoplasty. For example, the lenticules find use for a deep anterior lamellar graft, wherein the great majority of a recipient's corneal stroma has been removed; in some cases only Descemet's membrane and its associated endothelium remains. This is commonly referred to as a deep anterior lamellar keratoplasty (DALK). The lenticules also find use for a full thickness penetrating keratoplasty, wherein the entire thickness of a recipient's cornea is removed prior to graft placement. The lenticule design, instruments and procedures enable placement of a graft that exceeds the diameter of the recipient bed and will minimize or obviate the need for sutures. Other applications include the insertion of deformable materials for use in drug delivery and transplantation of cells integrated onto the surface or embedded within a deformable matrix. A deformable matrix is exemplified by but not limited to biologic, biosynthetic and synthetic polymeric materials.

SUMMARY

In one aspect, the invention provides a deformable object for implantation (e.g. cornea replacement lenticule), comprising a central region and a skirt, wherein the central region is configured to fit into a smaller diameter recipient bed and the skirt is configured to slip into a larger diameter stromal pocket located deep to the narrower superficial aspect of the surgical site and encircling the recipient bed. Deformable objects include but are not limited to 1. tissues for use in reconstructive surgery, 2. deformable polymeric materials such as hydrogels. Polymeric materials can be used for controlled drug delivery as well as for delivery of cells. In some embodiments involving corneal tissue, the lenticule is composed of native corneal tissue.

In a related aspect, the invention provides a cornea replacement lenticule, comprising a central region and a skirt, wherein the central region is configured to fit into a recipient bed for the cornea replacement lenticule, and the skirt is configured to slip into a stromal pocket encircling the recipient bed. In some embodiments, the lenticule is composed of native corneal tissue. In some embodiments, the lenticule is composed of biosynthetic or synthetic material. In some embodiments, the central region and the skirt are composed of the same material. In some embodiments, the central region and the skirt are composed of different material. In some embodiments, the diameter of the skirt is from about 1.1-fold to about 2.5-fold the diameter of the recipient bed. In some embodiments, the skirt has a diameter from about 6 mm to about 12 mm. In some embodiments, the thickness of the skirt is from 50-400 microns. In some embodiments, the skirt is positioned near the anterior surface of the recipient bed. In some embodiments, the skirt is positioned near or coincident with the mid-level of the recipient bed. In some embodiments, the skirt is positioned near or coincident with the posterior surface of the recipient bed. In some embodiments, the lenticule is coated with a bioactive ligand and/or an antibiotic. In some embodiments, the lenticule is as depicted in any one of FIG. 2, 3, 4 or 5.

In another aspect, the invention provides a surgical insertion device comprising a handle connected to a guide assembly, the guide assembly comprising:

(i) a mechanism to mechanically alter the radius of curvature and thereby the effective arc chord diameter of the object to be implanted allowing it to be passed through a the superficial aspect of the surgical site that has a lesser diameter than the object in its undeformed or relaxed state of maximum diameter. In some embodiments the deformation is accomplished by pressing the object to be implanted between two surfaces. In some embodiments the upper surface two prongs that assist in folding a cornea replacement lenticule into a desired shape by mechanically deforming the object to be implanted against a surface of lesser diameter and/or radius of curvature, wherein the handle contains a cylindrical hole(s) that serves as the track for a rod connected to the prongs which is used to exert mechanical force to change the effective diameter of the object to be implanted;

(ii) a conforming shell into which the object to be implanted can be mechanically deformed to assume the lesser radius of the conforming shell and to which the deformable object is maintained in contact with the conforming shell (being held in the desired form and radius of curvature) through mechanical; friction or through suction delivered to the deforming shell through a suction line attached to the top, allowing for the deformable object to be implanted to be held in the desired form, positioned into the surgical site (exemplified by but limited to the cornea), and then released; and (iii) a curved guide positioned under the shell, the guide having an arc for folding the lenticule over the top for guiding insertion of the lenticule into a recipient bed; wherein the insertion device conforms an object to be implanted as described herein into a shape of a smaller arc diameter to fit into a surgically prepared recipient bed having a superficial diameter that is less than the full relaxed diameter of the object to be implanted and places said object into a stromal pocket of greater diameter, capable of accommodating the full relaxed diameter of the object to be implanted encircling and located deep to the narrower superficial opening of the surgically prepared recipient bed. In some embodiments, the conforming shell is in the shape of an ellipsoid or a tulip having between three to 10 nodes. In some embodiments, the number of nodes is four. In some embodiments, the suction shell is an ellipsoid as depicted in any one of FIG. 10, 11A, 11B or 11C. In some embodiments, the conforming shell, also referred to as a tulip having four nodes as depicted in any one of FIG. 12, 13 or 14. In some embodiments, the insertion device is as depicted in any one of FIG. 6, 7 or 8. In some embodiments, the curved guide allows folding of the object to be implanted such that the arc chord diameter is less than the diameter of the superficial aspect of the surgically prepared recipient bed.

In a related aspect, the invention provides a cornea insertion device comprising a handle connected to a guide assembly, the guide assembly comprising:

(i) two prongs that assist in folding a cornea replacement lenticule into a desired shape, wherein the handle comprises a cylindrical hole that serves as the track for the prongs;

(iii) a suction shell positioned under the prongs, the shell comprising a suction line attached to the top, allowing for the lenticule to be held in the desired form, positioned in the eye, and then released; and (iv) a curved guide positioned under the shell, the guide having an arc for folding the lenticule over the top for guiding insertion of the lenticule into a recipient bed;

wherein the insertion device conforms a corneal replacement lenticule as described herein into a shape of a smaller arc diameter to fit into a cornea recipient bed and places the lenticule skirt into a stromal pocket encircling the recipient bed. In some embodiments, the suction shell is in the shape of an ellipsoid or a tulip having four nodes. In some embodiments, the suction shell is an ellipsoid as depicted in any one of FIG. 10, 11A, 11B or 11C. In some embodiments, the suction shell is a tulip having four nodes as depicted in any one of FIG. 12, 13 or 14. In some embodiments, the insertion device is as depicted in any one of FIG. 6, 7 or 8. In some embodiments, the curved guide allows folding of the lenticule such that the arc diameter is less than the arc diameter of the superficial aspect of the recipient bed.

In a further aspect, the invention provides a method of surgically reconstructing the cornea comprising:

(a) removing native cornea tissue, thereby creating a recipient bed for a replacement cornea;

(b) creating a stromal pocket encircling the recipient bed; and (c) inserting a corneal replacement lenticule as described herein into the recipient bed and stromal pocket using a cornea insertion device as described herein, wherein the lenticule in its relaxed state of maximal diameter has a diameter that exceeds the diameter of the recipient bed, and wherein the insertion device allows folding of the lenticule such that the radius of curvature and arc diameter (in at least one plane) is less than the diameter of the superficial aspect of the recipient bed and facilitates insertion of the corneal lenticule through the superficial aspect of the surgically prepared site into the stromal pocket encircling the recipient bed. In some embodiments, the majority of a recipient's corneal stroma has been removed. In some embodiments, only Descemet's membrane and its associated endothelium remains. In some embodiments, the entire thickness of a recipient's cornea has been removed. In some embodiments, the surgical procedure is performed without the use of sutures.

In a further aspect, the invention provides a method of replacing a cornea comprising:

(a) removing native cornea tissue, thereby creating a recipient bed for a replacement cornea;

(b) creating a stromal pocket encircling the recipient bed;

(c) inserting a corneal replacement lenticule as described herein into the recipient bed and stromal pocket using a cornea insertion device as described herein, wherein the lenticule has an arc diameter that exceeds the diameter of the recipient bed, and wherein the insertion device allows folding of the lenticule such that the arc diameter is less than the diameter of the superficial aspect of the recipient bed and facilitates insertion of the corneal lenticule into the stromal pocket encircling the recipient bed. In some embodiments, the majority of a recipient's corneal stroma has been removed. In some embodiments, only Descemet's membrane and its associated endothelium remains. In some embodiments, the entire thickness of a recipient's cornea has been removed. In some embodiments, the method is performed without sutures.

In another aspect, the invention provides an air insufflation needle comprising a portion of thick diameter and a portion of thin diameter, wherein the transition from thick diameter to thin diameter is an abrupt taper or step in the diameter of the needle that serves to increase the air tight seal of the needle. In some embodiments, the portion of thick diameter is 24 gauge and the portion of thin diameter is 30 gauge. In some embodiments, the entire length of the needle is straight. In some embodiments, the needle is bent at an angle within the thick portion. In some embodiments, the angle within the thick portion is 45°. In some embodiments, the length of the thin portion is about $\frac{1}{10}$th the length of the thick portion. In some embodiments, the needle is as depicted in FIG. 16.

In a further aspect, the invention provides a deforming device that enables the surgical implantation of a deformable object of greater diameter through and/or into a surgical site of lesser diameter. In some embodiments, the object of greater diameter is a corneal lenticule (embodiments of the corneal lenticule are as described herein). In some embodiments, the object of greater diameter is a controlled drug delivery polymeric device or a device used for the delivery of cells and/or tissues into the surgical site that are integrated on the surface or into the matrix of a deformable object.

In a related aspect, the invention provides a device that alters the radius of curvature of an object to be implanted into a surgical site such that the radius of curvature and arc chord diameter of the object to be implanted is decreased by contact with the device. In some embodiments, the arc chord diameter of the object to be implanted, once deformed from its resting or relaxed state using the device is equal to or less than the diameter of the superficial aspect of the surgical site into which the object is to be implanted. In some embodiments, the curvature is altered in only one plane with the orthogonal curvature and arc chord diameter remaining unaffected (depicted in FIG. 17). In some embodiments, the radius of curvature and arc chord diameter of the object to be surgically implanted is decreased by use of mechanical means. In some embodiments, single or multiple object surfaces are pressed against the object to be implanted forcing it to conform against a second and distinct surface of the device possessing lesser curvature and/or diameter than the object to be implanted. In some embodiments, the surface pressed against the object comprises two prongs. In some embodiments, the surface pressed against the object comprises a ring. In some embodiments, the surface pressed against the object to be implanted comprises a single surface that forces the object to be implanted against a second device surface to assume a lesser radius of curvature and arc chord diameter. In some embodiments, the radius of curvature and arc chord diameter of the object to be implanted is decreased by means of deformation against a single surface and maintained in that position by use of suction. In some embodiments, the radius of curvature and arc chord diameter of the object to be implanted is altered 360 around its circumference. In some embodiments, the object to be implanted achieves the desired decreased arc chord diameter by being introduced into a shape conforming shell. In some embodiments, the shape conforming shell has 3-10 nodes. In some embodiments the shape conforming shell has 3-6 nodes, in some embodiments the shape conforming shell has 4 nodes. In some embodiments, the object to be implanted is inserted into the shape conforming shell by mechanical means. In some embodiments, a separate insertion tool is used to position and insert the object to be implanted into the conforming shell. In some embodiments, the insertion tool has a surface curvature upon which rests the object to be inserted and through which a centered inserting plunger passes to mechanically insert the object to be implanted into the conforming shell. In some embodiments the object to be implanted is maintained within the shell by mechanical friction. In some embodiments, the object to be implanted is introduced and/or maintained within the conforming shell by vacuum. In some embodiments, the object to be implanted is introduced through the surgical site of lesser diameter into a stromal pocket of greater diameter by means of a mechanical plunger. In some embodiments, the object to be implanted is introduced through the surgical site of lesser diameter into a stromal pocket of greater diameter by means of a release of vacuum and/or application of positive pressure. In some embodiments, a footplate extends outward beyond the object to be implanted to assist with insertion of the object to be implanted through a surgical site of lesser diameter into a stromal pocket of greater diameter. In some embodiments, the outer diameter of the footplate slightly exceeds the superficial aspect of the surgical site allowing the footplate to be introduced into a deeper surgically created stromal pocket of greater diameter that was created to receive and accommodate the full (relaxed) diameter of the object to be implanted.

In another aspect, the invention provides a deformable object to be introduced through a surgical site of lesser diameter into a stromal pocket of greater diameter. The deformable object to be implanted achieves a lesser radius of curvature and arc cord diameter through interaction with the device. In some embodiments, the object is a corneal replacement lenticule (embodiments of the corneal replacement lenticule are as described herein).

In a further aspect, the invention provides a kit comprising one or more of:
i) a cornea replacement lenticule as described and depicted herein;
ii) a cornea insertion device as described and depicted herein;
iii) a air insufflation needle of any one of claims 25 to 31;
iv) a device that alters the radius of curvature of an object to be implanted into a surgical site as described and depicted herein;
v) a lenticule as depicted in FIG. 3, 4 or 5;
vi) an insertion device as depicted in FIG. 6, 7 or 8;
vii) a guide as depicted in FIG. 9;
viii) a suction device as depicted in FIG. 10, 11 or 15;
ix) a tulip device as depicted in FIG. 12, 13 or 14;
x) an air insufflation needle as depicted in FIG. 16;
xi) a forceps or implant delivery tweezer as depicted in FIG. 18 or 20;
xii) a reverse forceps or implant delivery tweezer as depicted in FIG. 19, 21 or 22; and/or
xiii) a device that alters lenticule curvature to facilitate delivery of a corneal lenticule as depicted in FIG. 23.

BRIEF DESCRIPTION OF THE DRAWINGS

FIG. 7 illustrates several views of an insertion device.

FIG. 14 illustrates tulip conforming devices.

FIG. 17 illustrates use of a device that alters the radius of curvature and arc chord diameter in corneal reconstructive surgery using a corneal lenticule and encircling skirt (of thinner dimensions) such that the encircling skirt is located ½ way along the axis of the thicker optical core ("mid-hat" configuration). In this specific example, a deep central wound bed is created that extends to the level approximating Descemet's membrane. An extension of the encircling stromal pocket is made at approximately halfway along the axial length of the wound created. An asymmetrically placed extension of this encircling stromal pocket is made at the same level within the stroma such that, after introduction of the corneal lenticule, it can accommodate the full diameter of the implanted lenticule in "relaxed" form of maximal diameter. The lenticule is then introduced using the surgical device, that in this case, decreases the radius of curvature and arc chord diameter of the corneal lenticule in only one plane with the diameter in the orthogonal plane having the normal full relaxed diameter. After being inserted into the deeper asymmetrically placed stromal pocket of greater diameter that accommodates the full diameter of the relaxed corneal lenticule, it is then re-positioned to allow the thicker central optic to "pop" into place while the encircling skirt of thinner dimensions occupies the encircling stromal pocket that was created.

DETAILED DESCRIPTION

1. Introduction

The Deformable Object (e.g., Lenticule):

Composition: In various embodiments, the deformable object can be tissue, biosynthetic or synthetic materials. The deformable object can be used in tissue reconstruction, delivery of therapeutic agents or delivery of integrated tissues and/or cells. In some embodiments using tissue for reconstructive purposes, exemplified by but not limited to corneal tissue, lenticules that can be made of native corneal tissue harvested from the same individual (autograft), the same species (allograft) or different species (xenograft); or can be a biosynthetic (e.g., having at least some element of biologically derived constituents, exemplified by but not limited to proteins such as collagen, (e.g., collagen I, collagen IV), laminin, fibronectin and proteoglycans) or completely synthetic (e.g., comprised of materials including but not limited to hydrogels, polymethylmethacrylate (PMMA), poly-2-hydroxyethyl methacrylate (pHEMA), poly (ε-caprolactone) (PCL), polyvinyl alcohol (PVA), Glass-reinforced hydroxyapatite (GRHA) and mixtures thereof). Synthetic or artificial corneas are known in the art (e.g., Boston keratoprosthesis (KPro), AlphaCor™) and find use. In one embodiment, the lenticule is a Boston keratoprosthesis (KPro), e.g., an aphakic optic with a diameter in the range of 7.0-8.5 mm comprised of polymethylmethacrylate (PMMA). In one embodiment, the lenticule is an Alpha-Cor™, e.g., a synthetic cornea measuring 7.0 mm in diameter and 0.5 mm in thickness, comprised of a peripheral skirt and a transparent central region connected by an interpenetrating polymer network made from poly-2-hydroxyethyl methacrylate (pHEMA).

In various embodiments, the lenticules can have a uniform composition throughout its thickness or can be a laminate (differing materials) in composition varying in a radial and/or axial orientation. The central core and the skirt of the lenticule can be composed of the same or of distinct materials. In one embodiment, the lenticule is an artificial cornea comprised of plasma-treated electrospun poly (ε-caprolactone) (PCL) nanofibers, attached to a hydrogel disc of polyvinyl alcohol (PVA) as a central optical part (see, e.g., Bakhshandeh, et al., *Int J Nanomedicine.* (2011) 6:1509-15). In varying embodiments, the skirt of the lenticule comprises titanium oxide ($TiO_2$) and/or hydroxyapatite (HA) (see, e.g., Tan, et al., *J Mater Sci Mater Med.* (2012) 23(4):1063-72). Further biologically derived and synthetic materials useful in constructing replacement lenticules are described, e.g., in Ruberti, et al., *Annu Rev Biomed Eng.* (2011) 13:269-95; Hartmann, et al., *J Biomed Mater Res B Appl Biomater.* (2011) 98(1):8-17; Santos, et al., *Invest Ophthalmol Vis Sci.* (2011) 52(7):4274-81; Ma, et al., *J Mater Sci Mater Med.* (2011) 22(3):663-70, Pino, et al., *Acta Biomater.* (2008) 4(6):1827-36; and Xu, et al., *J Biomater Sci Polym Ed.* (2008) 19(4):431-9.

Figure 1:
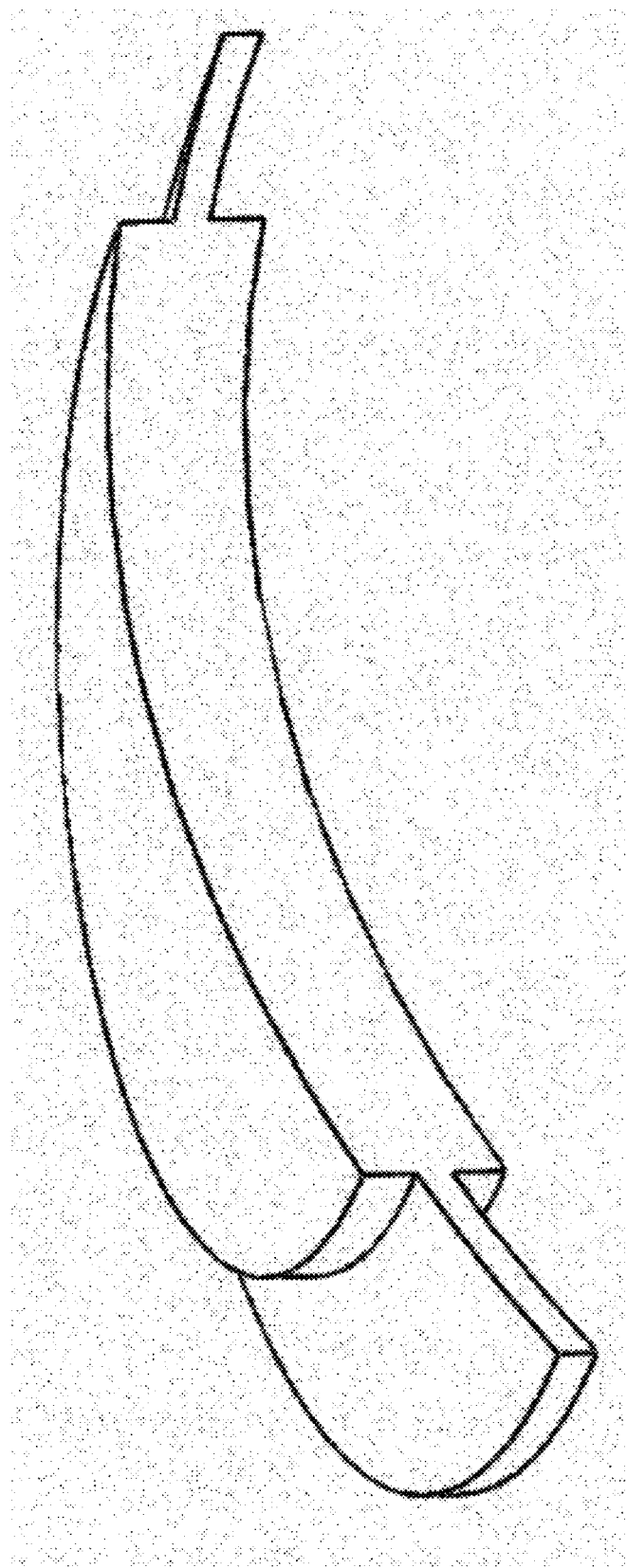
FIG. 1 illustrates a cross-section of one embodiment of deformable object geometry, exemplified by but not limited to a corneal lenticule, whereby the encircling skirt is located at approximately half way along the axial diameter of the central optical core, also referred to herein as a "midhat" lenticule geometry. The encircling skirt would be located in such as fashion as to be located within a corneal stromal pocket that was surgically constructed.
Figure 2:
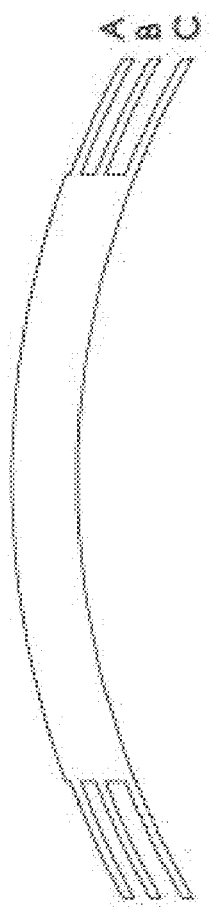
FIG. 2 illustrates varying possible positions of the skirt along the axial length of the thicker central core of a deformable object (exemplified by but not limited to the optical core of a lenticule). The location of the skirt in an anterior to posterior axis can vary from being located coincident with the anterior surface to being located coincident with the posterior surface.

Design: The present lenticules have an outer diameter that exceeds the diameter of the superficial aspect of the surgically created recipient bed. This is made possible by the creation of a recipient encircling pocket in the recipient cornea within the stroma. For example, if the recipient bed is 6 mm in diameter the lenticule diameter can range from 6.25 mm to 11 mm, with various embodiments ranging from 1 mm to 6 mm greater diameter (lenticule diameter>wound bed diameter) and some embodiments ranging from 1 mm-4 mm greater diameter (lenticule diameter>wound bed diameter). The lenticule will have a central region (optic) that is either the same diameter as the recipient bed or slightly greater (0.25 mm-2.0 mm greater). A slightly greater diameter ensures that lenticule tightly apposes the walls of the recipient bed. The thickness of the central optical element approximates the thickness of the recipient surgical bed. The skirt of the lenticule is the element that upon completion of the surgical procedure remains inserted into the encircling stromal pocket. The skirt can be composed of the same material as the central core or can be composed of a distinct biomaterial. The thickness of the skirt could vary from 10s of microns to 100s of microns with various embodiments ranging from 50-400 microns and some embodiments ranging from 75-300 microns. The location of the skirt in an anterior to posterior axis can vary from being located near the anterior surface to being located coincident with the posterior surface (FIG. 1; depicted by locations A, B, C). The optimal axial location of the skirt may vary with the surgical procedure being performed (lamellar keratoplasty, deep anterior lamellar keratoplasty referred to as DALK or penetrating keratoplasty referred to as PK). It is noted that in order for the skirt to insert into the lamellar pocket that it must reside behind the anterior surface of the lenticule if the anterior surface of the optical core element is to be coincident with the corneal surface. It is also noted that for some applications such as lamellar keratoplasty and DALK, the skirt can be coincident with the posterior surface of the lenticule.

The lenticule can be made from donor corneal tissue using a femtosecond laser to sculpt the design, can be sculpted using a femtosecond laser out of a synthetic or biosynthetic construct or can be molded using biologically derived, bioengineered, synthetic or biosynthetic materials. Additionally, the lenticule can be coated with bioactive ligands or other therapeutic agents such as antibiotics using ligation chemistries, polyelectrolyte multilayers, spincoating, electrospinning and the like. Bioactive ligands can also be integrated throughout the bulk of the lenticule through a variety of processes including simple admixture and integration using any of a number of ligation chemistries. The lenticule can be fabricated using a lamination process such that different materials are introduced along its thickness.

The present lenticules allow for minimizing or avoiding placement of sutures into natural, bioengineered, biosynthetic or synthetic constructs whose material properties may make them less than ideal for suture to be placed through them. Even in cases where the material that composes the lenticule were to hold suture well, minimizing or obviating suture placement can provide advantages such as less reactivity, increased patient comfort, minimal induction of astigmatism and faster biointegration.

Surgical Cornea Insertion Devices: Surgical instruments that conforms an artificial or donor cornea into a shape of a smaller radius of curvature and arc chord diameter such that it can be fit into the pre-cut surgically prepared bed in the cornea and that facilitate placement of the lenticule or encircling lenticule skirt into the stromal pocket. In varying embodiments, the surgical devices are comprised of stainless steel, plastic and mixtures thereof.

Figure 12:
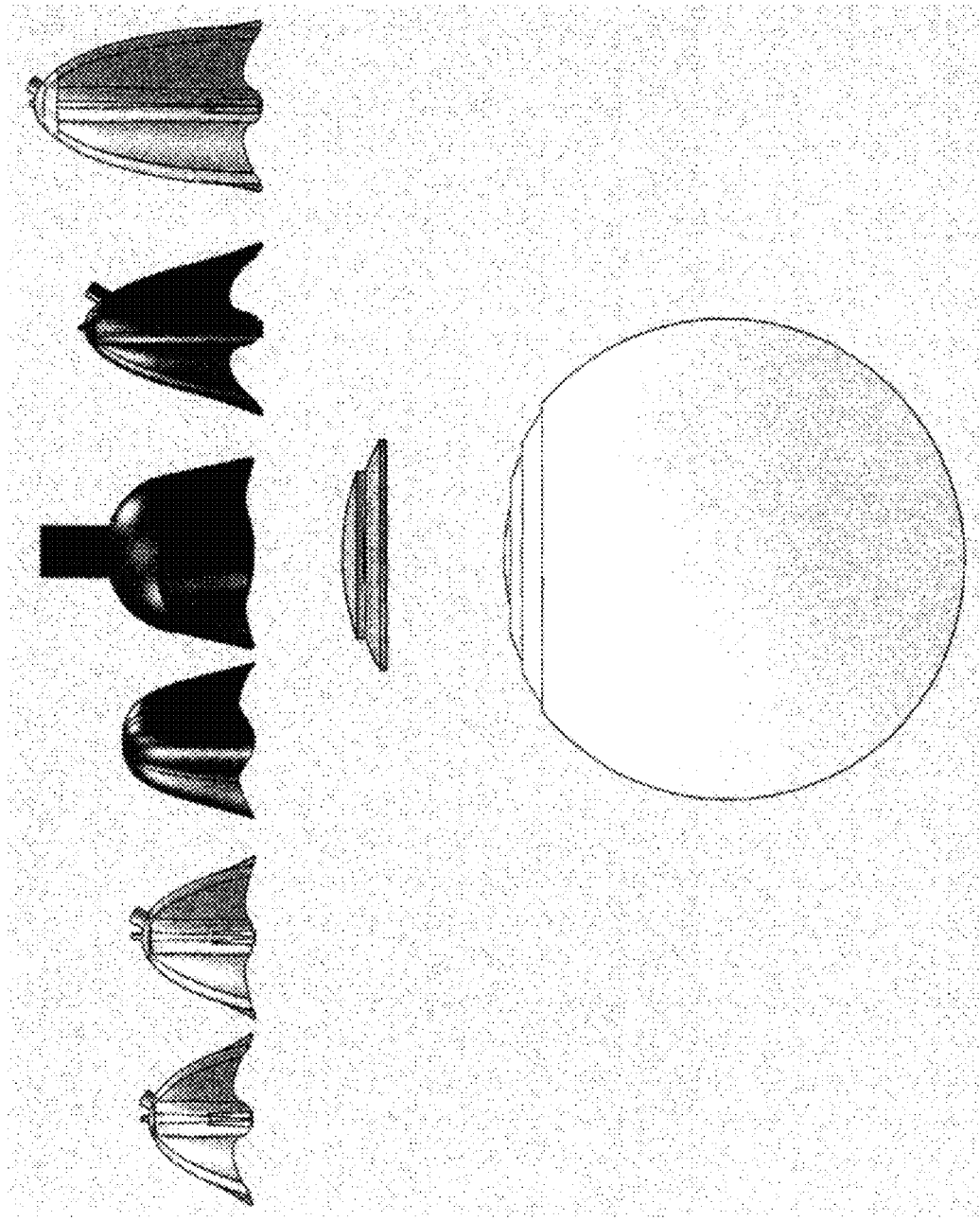
FIG. 12 illustrates "tulip" devices. This configuration of conforming device folds the implantable object to deformed into a geometry such that the arc chord diameter is less than the superficial aspect of the surgical wound site across the entire 360 degrees of the deformable object to be implanted. In such a configuration, the creation of an asymmetric stromal pocket is not required. Note that in certain embodiments of this conforming device the lenticule can be conformed to the devices using a "jig" to ensure centration. In other configurations a "rod" or "plunger" made of any relatively stiff natural or synthetic material could be used to firmly position the lenticule into the "tulip" conforming device.
Figure 13:
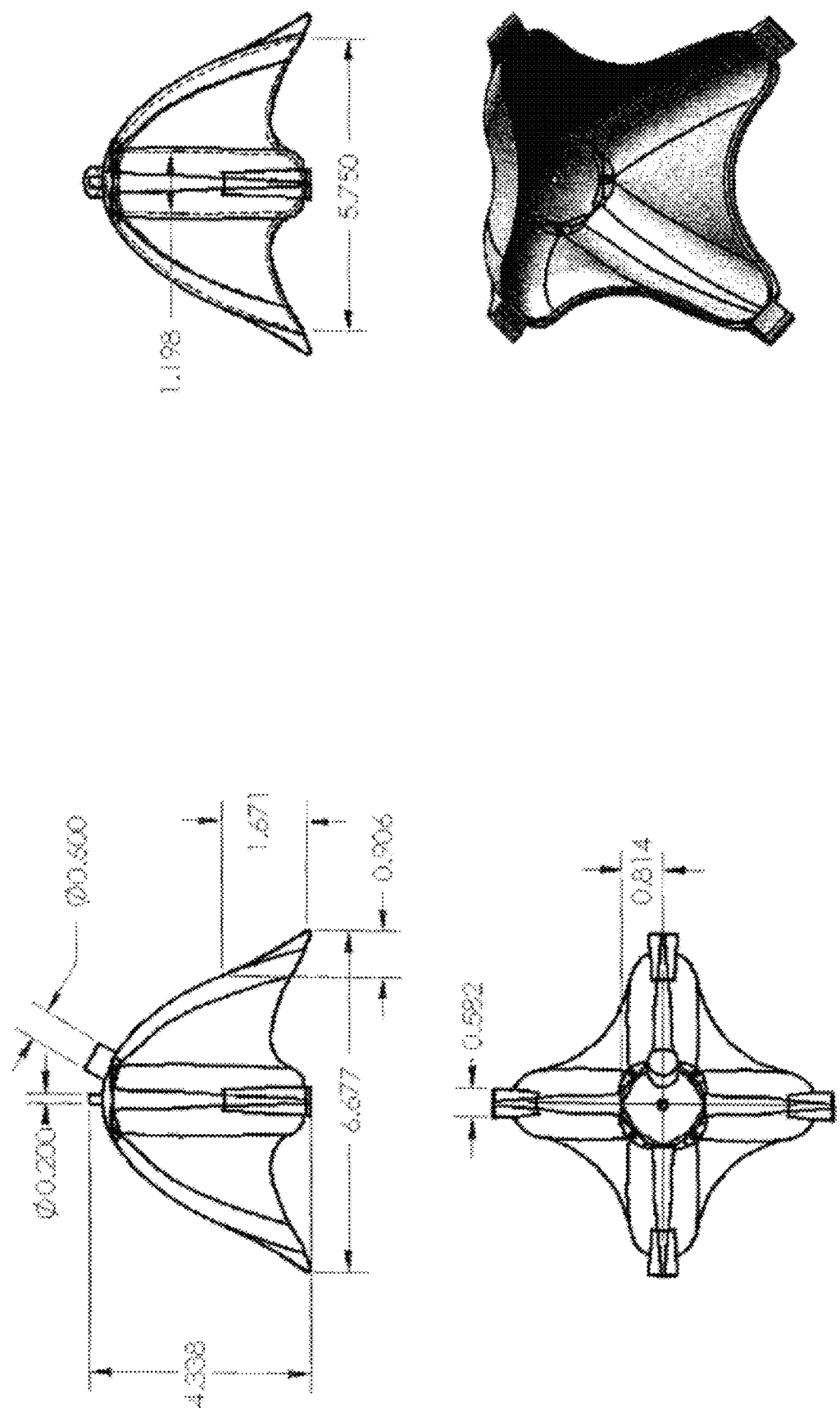
FIG. 13 illustrates tulip devices.

It is noted that the surgical devices fall into two broad categories:
1. Devices that fold the lenticule such that the arc diameter of the lenticule is decreased to less than that of the prepared surgical bed along one axis with the orthogonal axis maintaining the normal unfolded arc diameter, and
2. Devices that alter the arc chord diameter 360 degrees along the circumference of the folded lenticule such that the arc diameter of the lenticule is decreased to less than that of the prepared surgical bed. ("Tulip" designs—FIGS. 12-14).
Cornea Insertion Surgical Procedure: Corneal Wound Bed Preparation Lamellar keratoplasty: In this procedure, a superficial layer of the corneal stroma is excised, an encircling lamellar pocket is created and the corneal lenticule is implanted. There are several distinct approaches to implanting the lenticule that employ different unique surgical instruments. All of the devices that alter the radius of curvature and arc cord diameter, including the tulip designs, could be employed for lamellar, DALK and PK. When using devices that alter the radius of curvature and arc chord diameter in only one plane (with the orthogonal diameter remaining unaffected), an asymmetric stromal pocket must be made to enable seating of the entire full diameter of the relaxed lenticule into the asymmetric pocket and then re-positioning it such that the skirt is in the completely encircling stromal pocket. The asymmetric corneal pocket is extended outward from the smaller diameter encircling lamellar pocket and is an extension (in the same stromal plane) of the initial stromal pocket created. The large asymmetric stromal pocket extends into one quadrant of the corneal stroma and in some cases (depending on size of the surgical site and the size of the lenticule) may extend to the vicinity of the limbus. After being introduced into the stromal pocket and allowed to assume its full relaxed diameter, the lenticule is subsequently repositioned such that the thick central optical core fully occupies the deep central wound and the skirt is fully seated in the encircling stromal pocket. The devices that alter the radius of curvature and arc chord diameter along 360 degrees described herein do not require a large asymmetric pocket to be made. In these cases, the skirt is positioned simultaneously 360 degrees around into the encircling stromal pocket and the central core (optical) piece is not deposited into the stromal pocket.

DALK: In embodiments where DALK is performed, the corneal stromal tissue is removed to approximate the level of Descemet's membrane. In one embodiment of the procedure, a trephination of approximately 300 µm is made, a Suarez corneal spreader or other lamellar dissector is used to create an encircling stromal pocket of approximately 2 mm in lateral extent outward from the original surgical wound. The central 300 µm stromal button excised, air and/or viscoelastic placed in the vicinity of the deep stroma using a specially designed cannula in order to push Descemet's membrane back. The rest of the overlying corneal stroma is then sharply excised. The lenticule is then inserted into the stromal pocket using one of the specially designed tools described herein and positioned such that the skirt is in the encircling stromal pocket and the central (thicker) optic is in the wound bed demarcated by the initial trephination.

Penetrating Keratoplasty (PK): The entire thickness of the cornea is removed and the lenticule implanted. The devices described herein whereby the radius of curvature and arc chord diameter are decreased 360 degrees are especially suited to performing this procedure.

2. Detailed Embodiments a. Deformable Object to be Implanted

Deformable object to be implanted: The following are illustrative of the invention but it is clear to those skilled in the art of surgery and implantable objects that numerous embodiments in terms of object composition, object design and design of instruments are possible. In varying embodiments, the methods entail:
  1. Creation of a surgical wound bed in tissues exemplified by but not limited to the cornea with an encircling stromal pocket; and
  2. Use of specifically designed surgical instruments that: a) allow folding of the object to be implanted such that the arc diameter is less than the superficial diameter of the recipient wound bed and b) facilitate insertion of the deformable object to be implanted through the narrow superficial aspect of the surgical site into the larger encircling stromal pocket that accommodates the relaxed diameter of the object to be inserted.
  3. Use of a deformable object (e.g. corneal lenticule) whose arc diameter in the relaxed state exceeds the diameter of the recipient bed with a skirt that inserts into a lamellar pocket surrounding the recipient corneal wound bed that can assume an arc diameter that is ≤ (equal to or less than) the superficial aspect of the wound site through use of devices described in 2 above.

Figure 3:
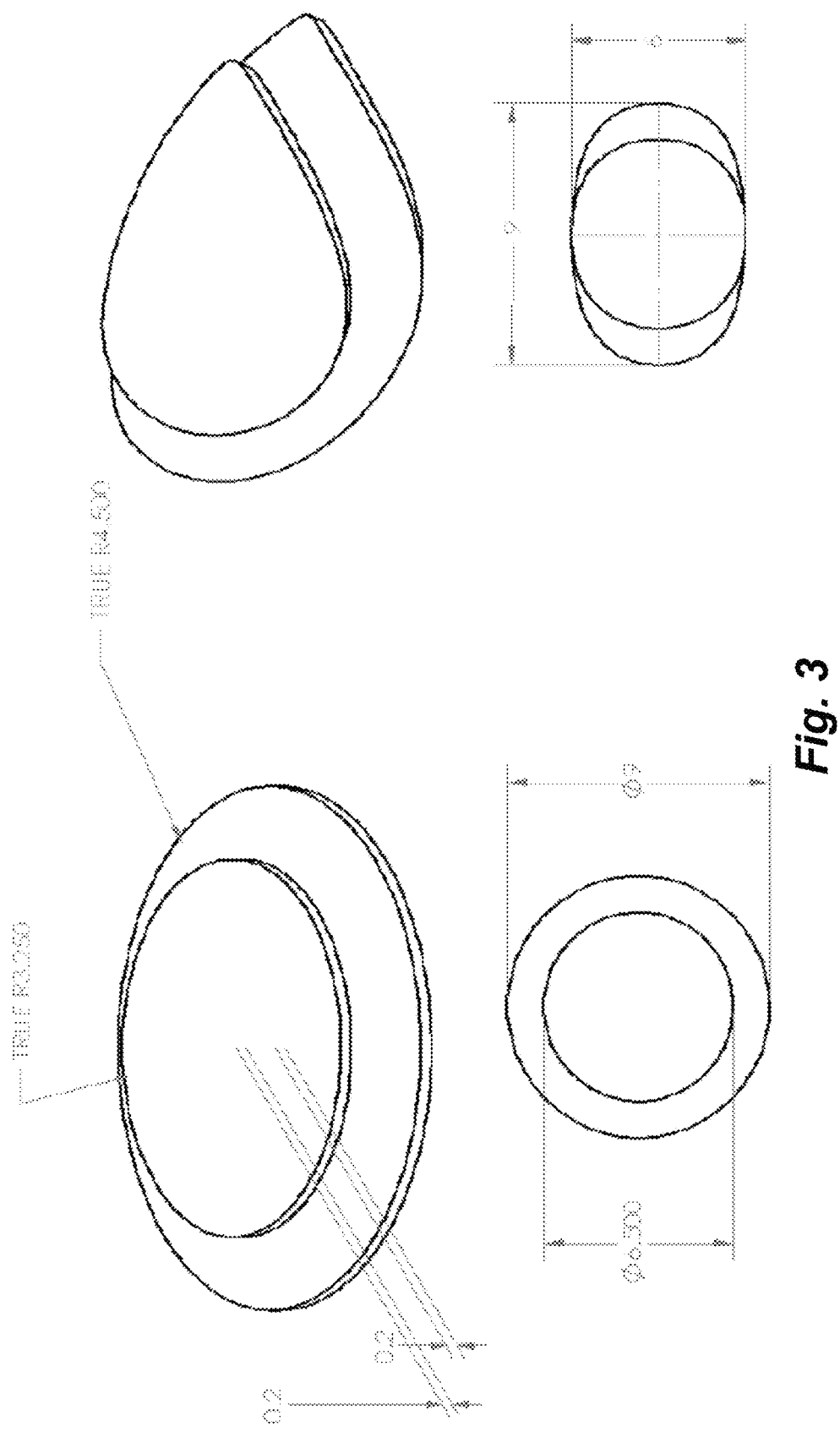
FIG. 3 illustrates lenticule designs before and after deformation.
Figure 4:
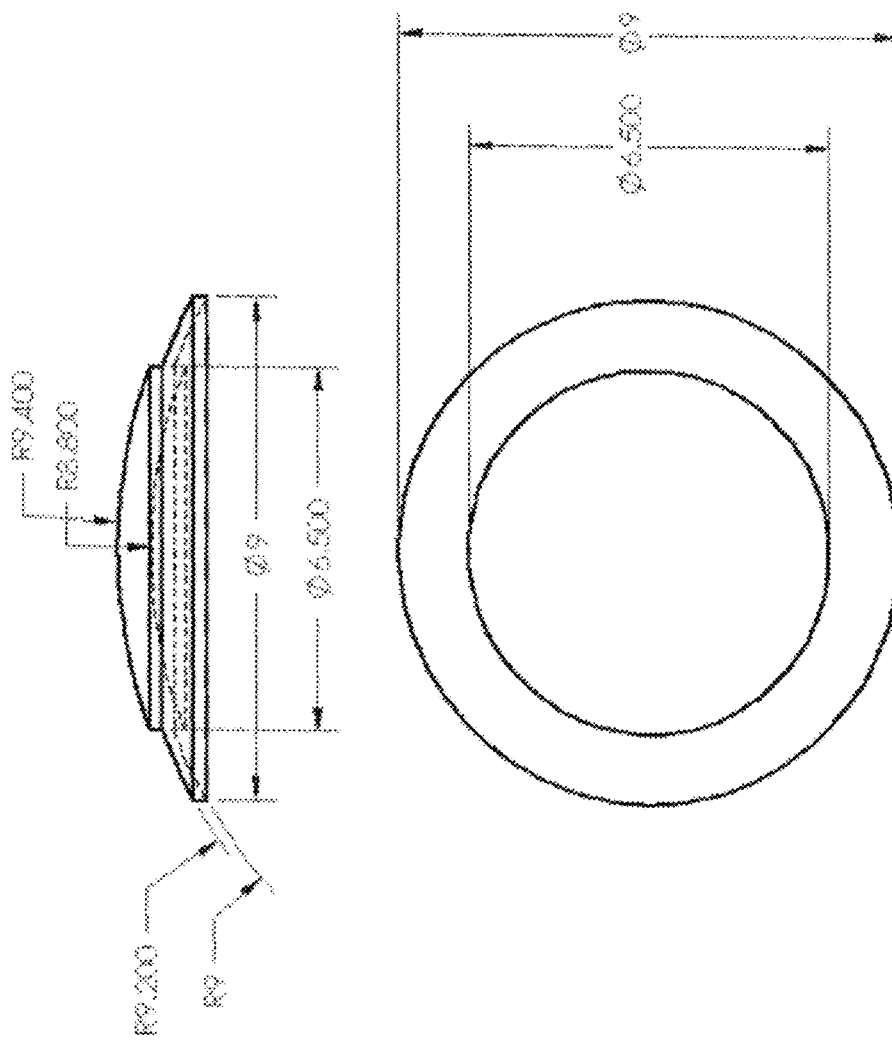
FIG. 4 illustrates lenticule designs with a total diameter of 600 μm.
Figure 5:
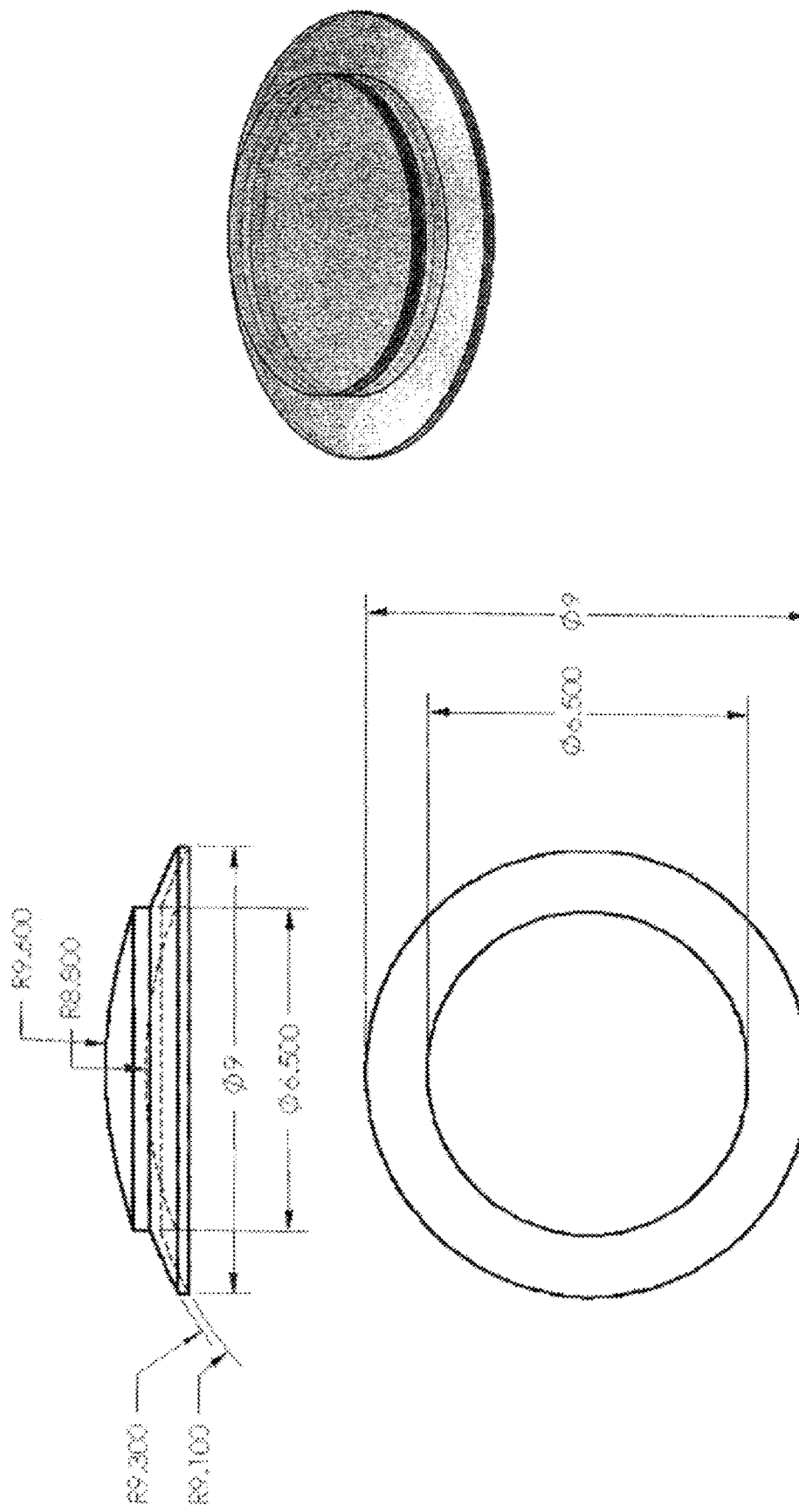
FIG. 5 illustrates lenticule designs with a total diameter of 800 μm.

In one illustrative example using the cornea, the recipient cornea has an approximate thickness of being 600 µm. A recipient bed of 6 mm diameter has been made using standard procedures for performing DALK surgery. In this case, the total diameter of the lenticule was chosen to be 9 mm, of which the central 6.5 mm has a thickness of 800 µm, while the outer skirt extends 1.5 mm out from the central core. The 800 µm thickness is determined by the native 600 µm thickness added to the skirt thickness of 200 µm (acts as a spacer within the stroma increasing the thickness needed for the core element to appose the full thickness of the stroma). The skirt region has a thickness of 200 µm. It should be noted that the central core may have a thickness that is approximately equal to the thickness of the recipient bed or may approximate the thickness of the recipient bed plus the skirt thickness. See, e.g., FIGS. 3-5.

b. Surgical Cornea Insertion Instruments i. Mechanical Insertion Device

The surgical insertion instruments are designed such that the object to be implanted (e.g. corneal lenticule) can be folded over the top to an arc width less than 6 mm then guided into the surgically prepared recipient bed where it then unfolds to the original diameter of 9 mm. The device is curved to an overall base curve of 8.8 mm to facilitate interaction with the eye during the surgical procedure. It should be noted that this curvature can vary depending on the purpose of the surgery, the nature of the implantable object, age of the recipient and the species on which the surgery is being performed.

Figure 6:
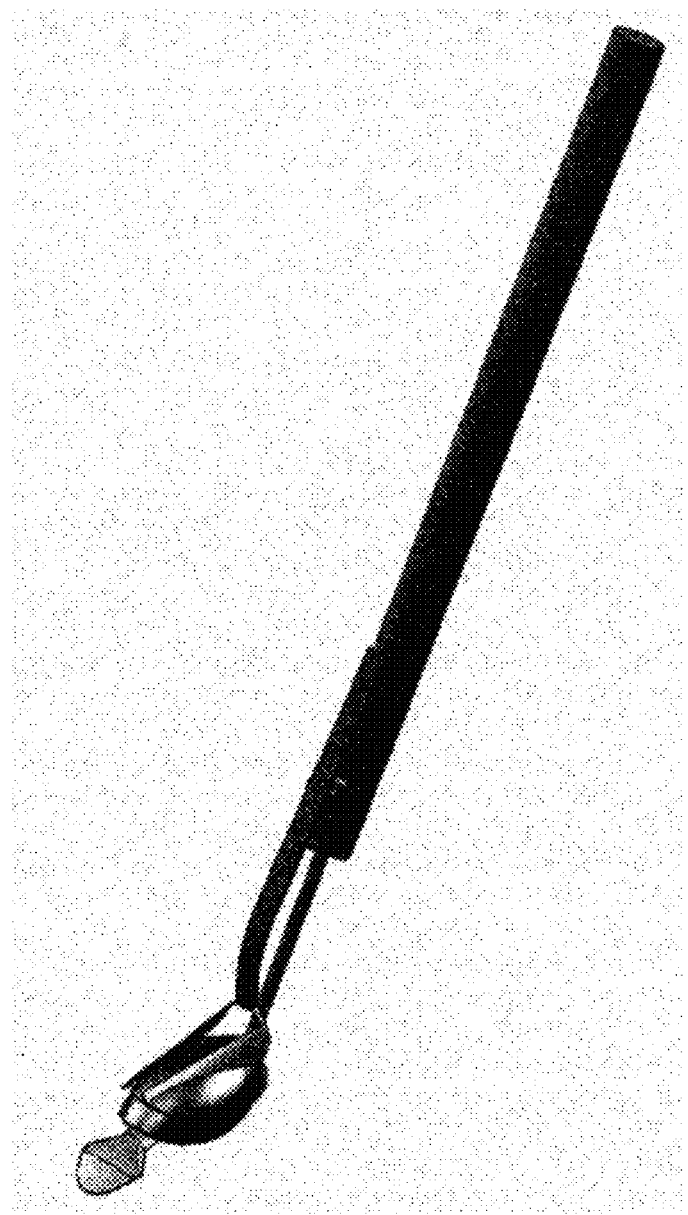
FIG. 6 illustrates an insertion device with a deformed lenticule.
Figure 8:
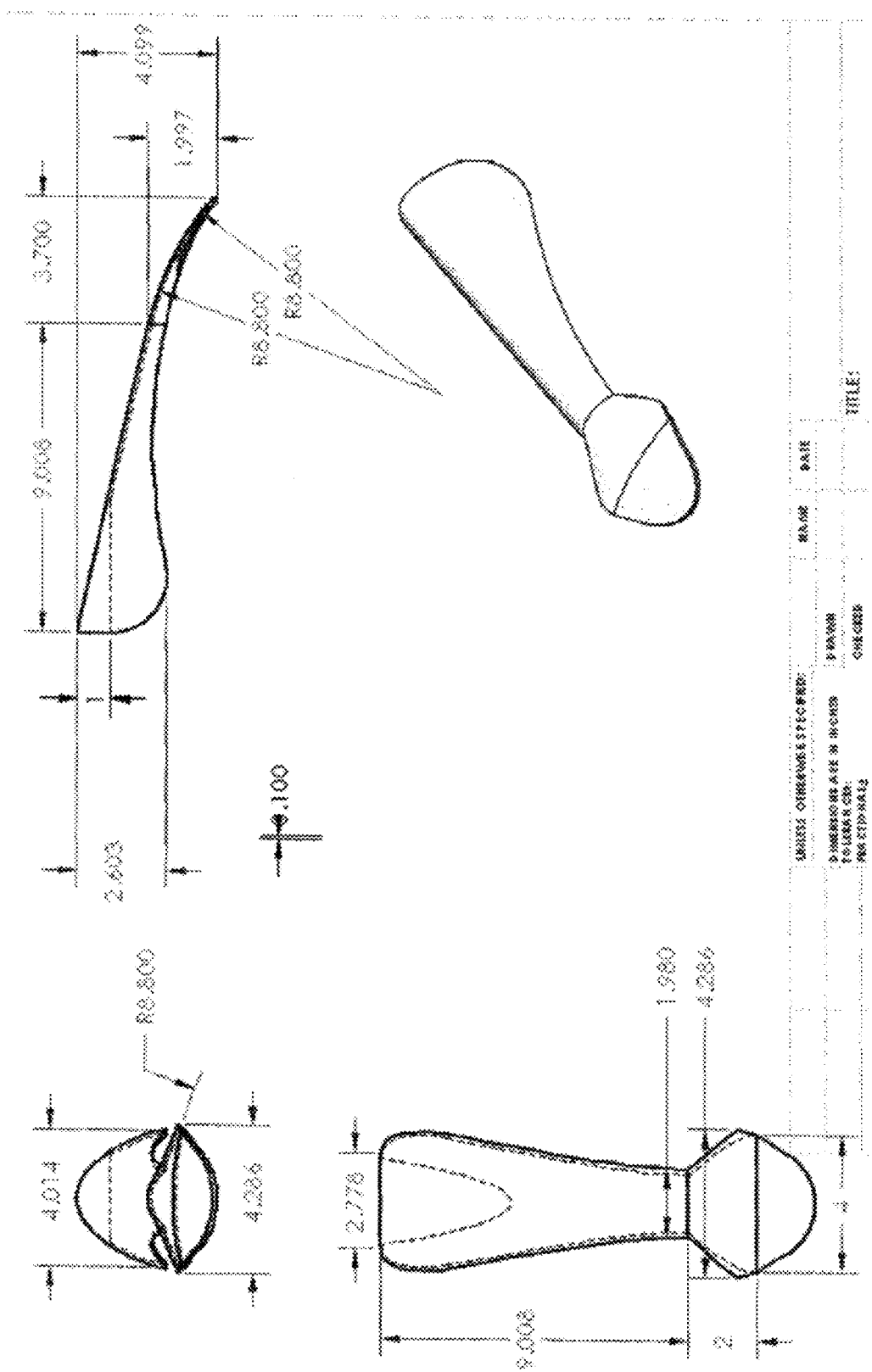
FIG. 8 illustrates the insertion piece of an insertion device.

Attached to the instrument are two prongs that assist in folding the lenticule to the desired shape. These prongs are moved up and down via a guide track, located inside the handle. The handle is a standard instrument handle, with the modification of a cylindrical hole that serves as the track for the prongs. The prongs mechanically deform the object against a lower surface having a smaller radius of curvature and/or diameter See, e.g., FIGS. 6-8.

ii. Suction Device Design

Figure 10:
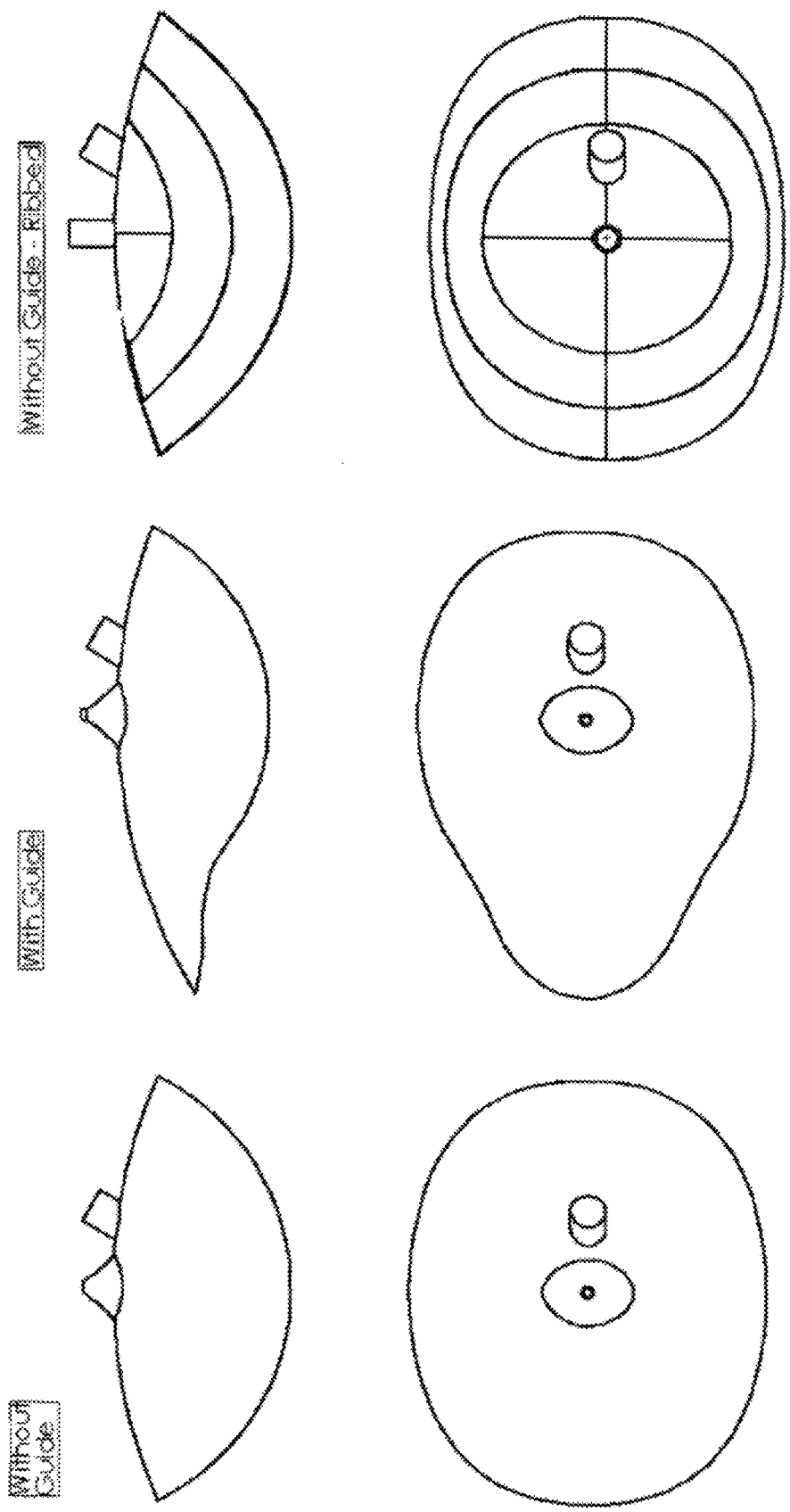
FIG. 10 illustrates suction devices.
Figure 11A:
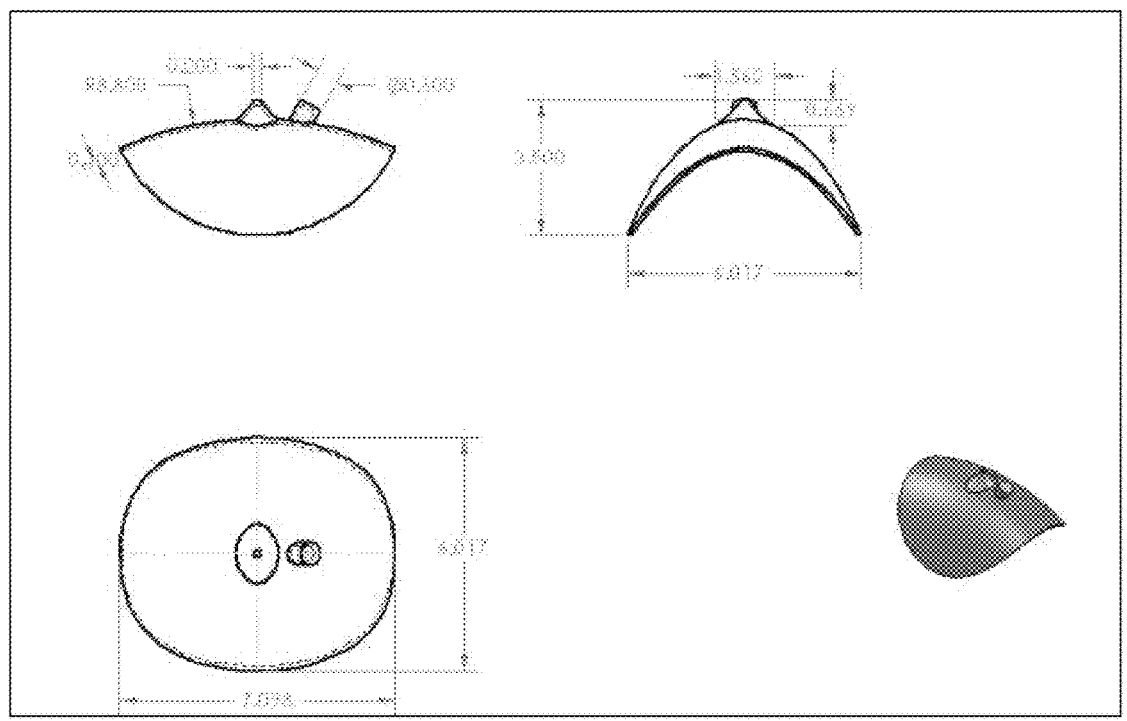
FIGS. 11A-C illustrate suction devices.
Figure 11B:
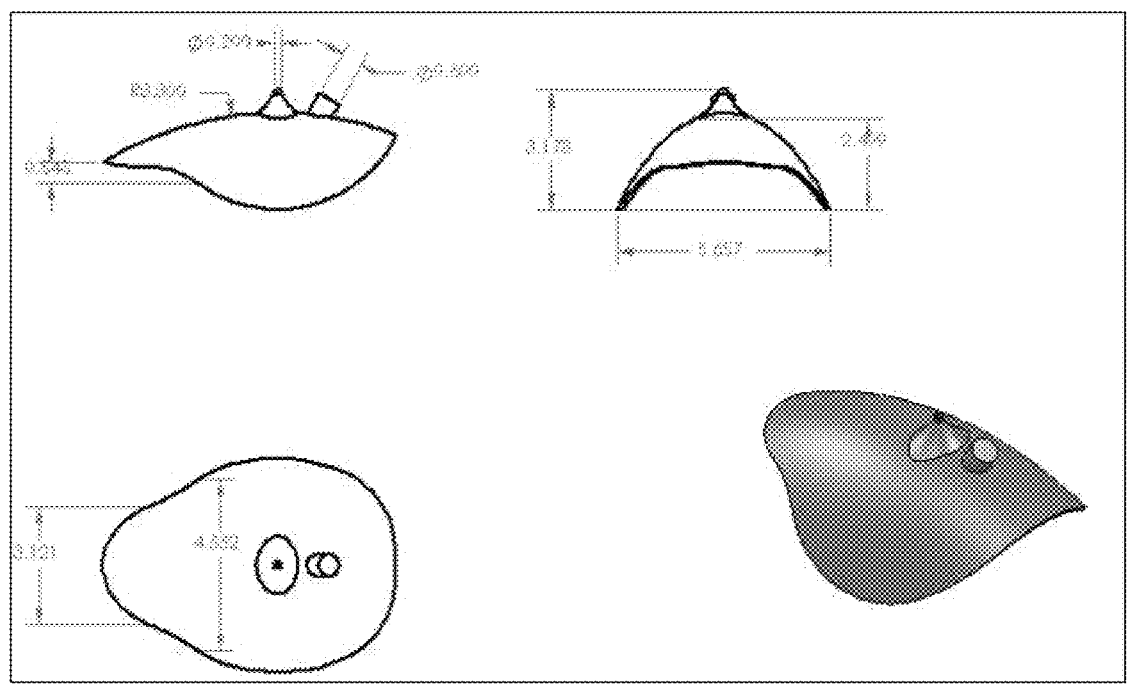
Figure 11C:
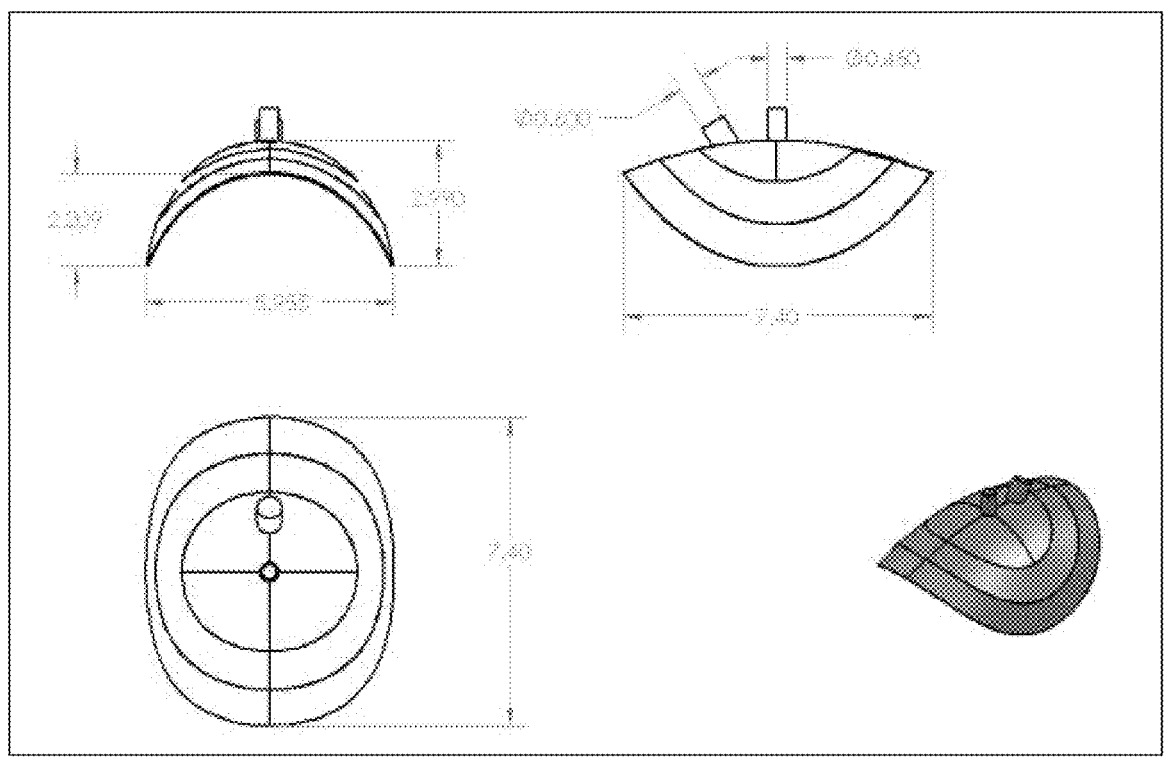
Figure 15:
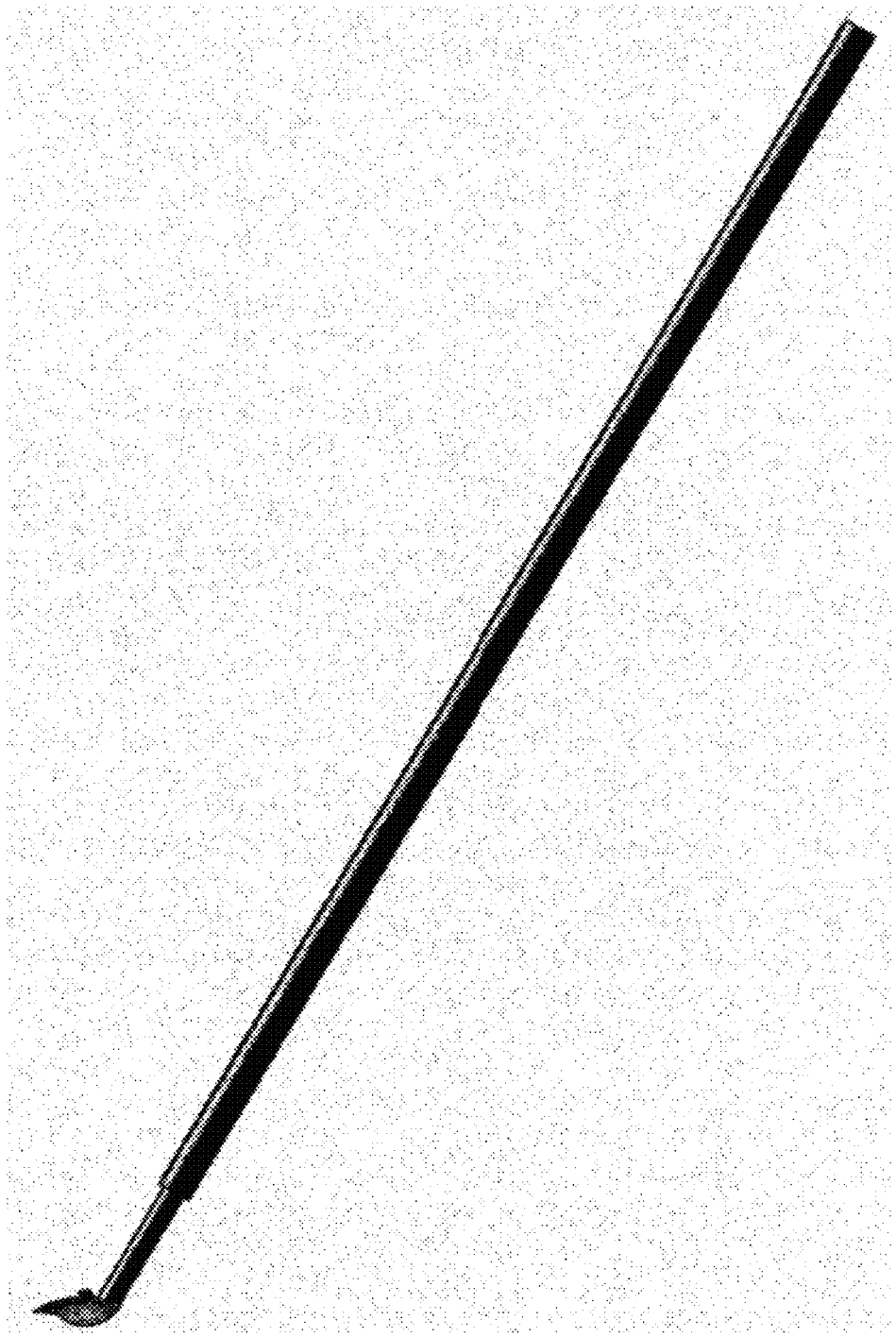
FIG. 15 illustrates a lower magnification view of a suction device.

The overall design of the suction devices is an ellipsoid shell with a suction line attached to the top. This would allow for the lenticule to be held in the desired form, positioned in the eye, and then released by releasing vacuum and/or forcing air into the suction line. The suction line can be attached during fabrication, and would comprise tubing (e.g., 1 mm diameter) attached to a luer lock medical syringe. A standard surgical instrument handle can be attached at the back of the suction device. See, e.g., FIGS. 10, 11 and 15.

iii. Mechanical Device—Simple Guide

Figure 9A:
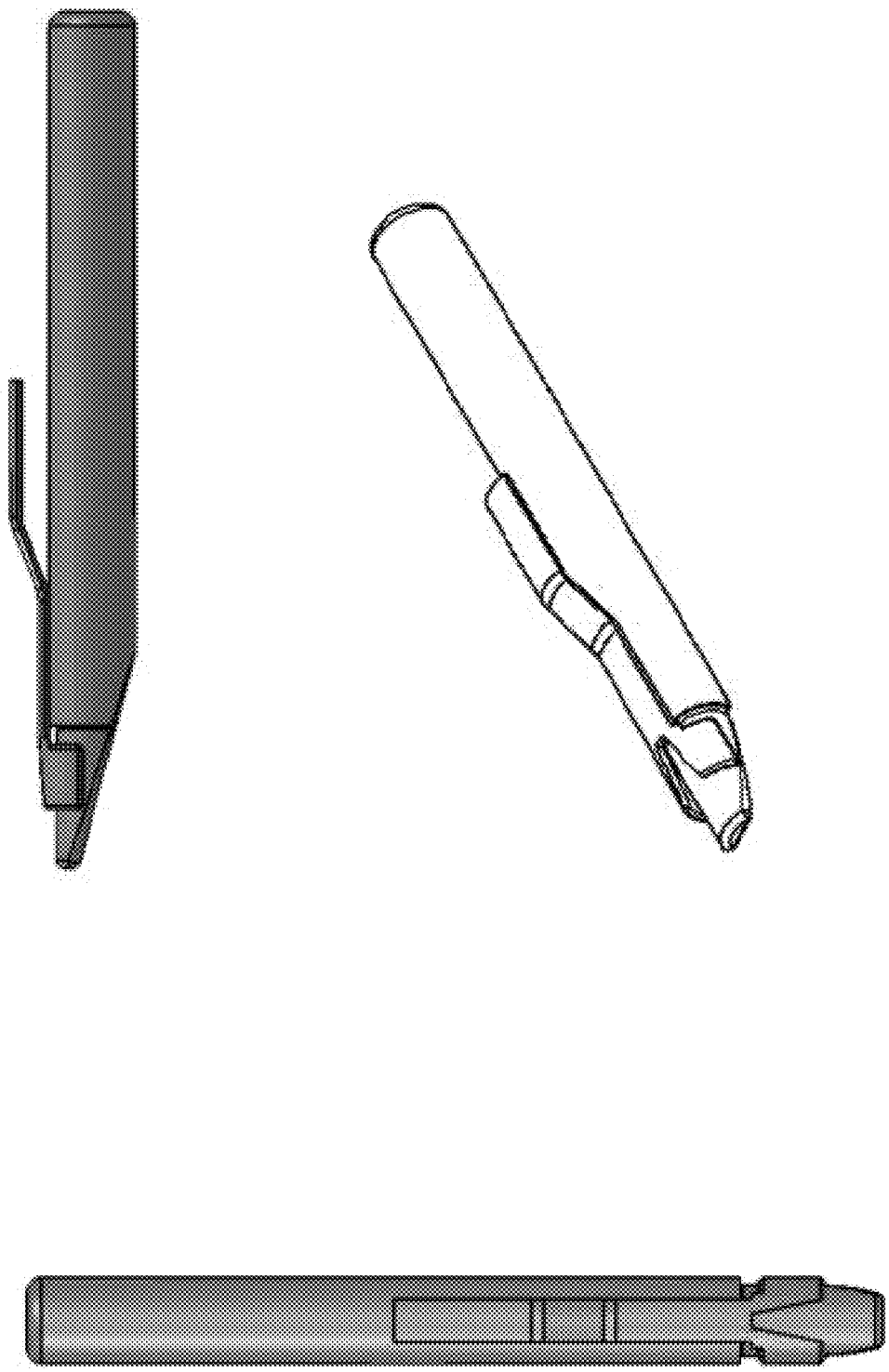
FIG. 9 illustrates a guide.
Figure 9B:
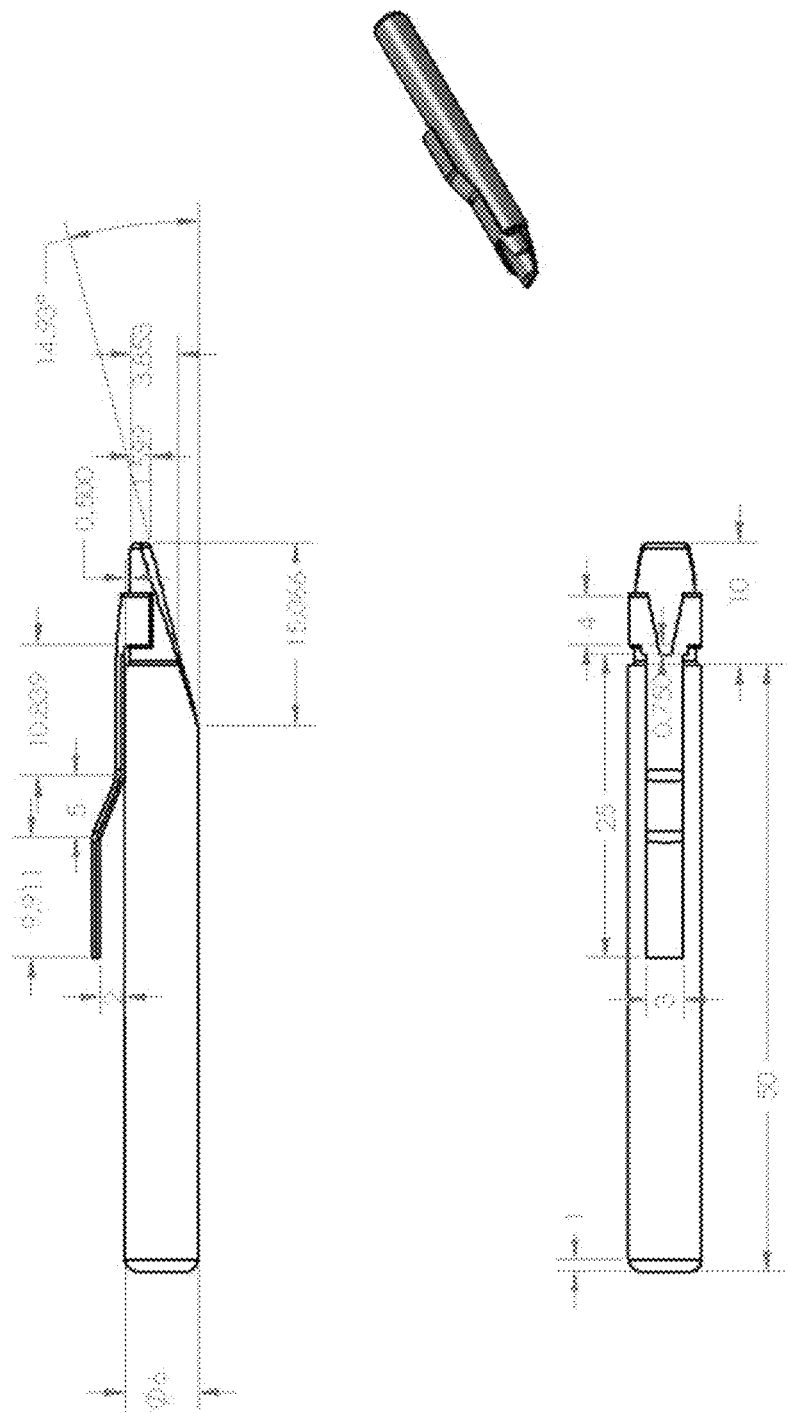

The simple guide mechanical device is designed to provide a cylindrical surface for the lenticule to be wrapped around to decrease its width and allow it to be inserted into the opening in the eye. It comprises two parts, a cylinder and a cylindrical clip above it, which can be attached by spring steel. See, e.g., FIGS. 9A-B.

iv. Tulip Device—Four Nodes

The tulip surgical device is designed to guide the lenticule into four folds such that its overall diameter is small enough to fit through the narrower superficial aspect of the surgical site, after which it is held in place using suction or intrinsic mechanical pressure created by the folded lenticule exerting pressure against the walls of the shaping receptacle (friction). The object to be implanted can be inserted into the shaping receptacle via mechanical insertion for example using a plunger device. The centering of the lenticule could use a jig to ensure centration. Then, after the lenticule has been positioned appropriately using the shaping/insertion devices the eye it can be released by releasing vacuum and/or pushing air into the suction line or by mechanically pushing the lenticule out of the delivery device (e.g., with a plunger). The suction line/plunger can be attached during fabrication. A standard surgical instrument handle can be attached at the back of the suction/mechanical shaping device.

An additional design feature of this device is the presence of 3 or more footplates (or even a completely encircling extension) that extend beyond the lenticule and whose outer diameter slightly exceeds the diameter of the superficial aspect of the surgical site. In this case, by introducing one or more of the footplates into the deeper stromal pocket and applying gentle pressure outward against the superficial wall, thus slightly deforming the wall and allowing the other footplates to and subsequently re-positioned such that all footplates reside within the encircling stromal pocket. By applying gentle upward pressure the footplate(s) could be used to dilate the stromal pocket facilitating delivery of the skirt of the lenticule into the stromal pocket 360 degrees around the wound bed. While the illustration depicts a four node design it will be obvious to those skilled in the art of surgery and creation of surgical instruments that many configurations are possible with 3-10 nodes being able to achieve the same result in terms of deforming the lenticule. Tulip devices are depicted, e.g., in FIGS. 12-14.

v. Air Insufflation Needle

Figure 16:
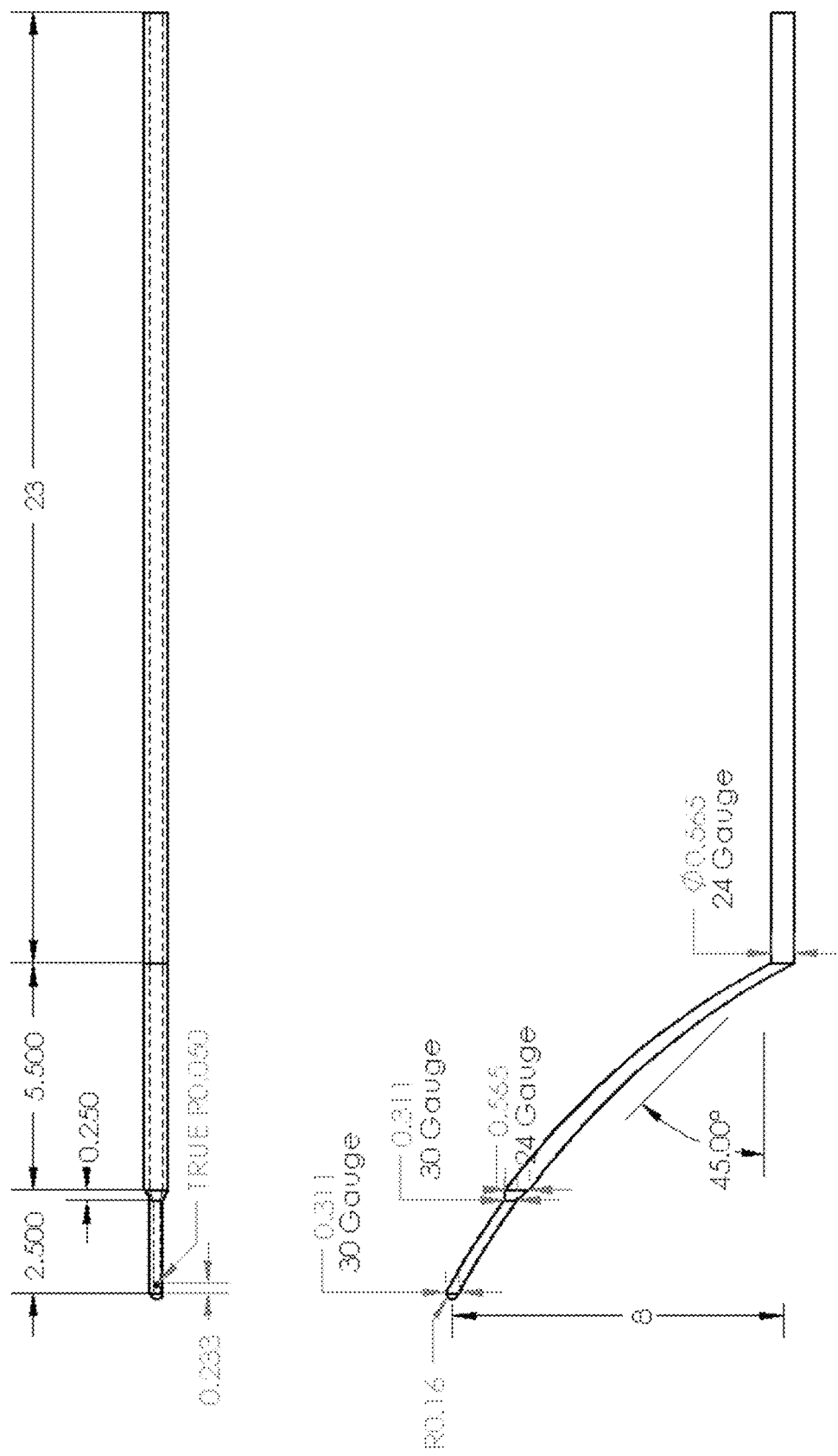
FIG. 16 illustrates an air insufflation needle, e.g., for performing a DALK big bubble surgery, showing an abrupt taper or step in the diameter of the needle that serves to increase the air tight seal of the needle (facilitating the formation of a bubble).

An air insufflation needle is a specialized needle used for deep anterior lamellar keratoplasty (DALK). This needle is used to introduce air or liquid to push Descemet's membrane posteriorly in what is referred to as the big bubble technique (see, e.g., video on the internet at youtube.com/watch?v=Aim1Lnp0hoc). The unique feature of the air insufflation needle depicted in FIG. 16 is the abrupt taper or step in the diameter of the needle that serves to increase the air tight seal of the needle (important for the formation of the big bubble). Note that the exact dimensions of the various elements of the needle can be altered and still be effective. Also please note that the step in the video that uses a blunt dissector prior to needle placement can be employed but is a not a requirement for use with the present needle.

vi. Kits

Figure 18:
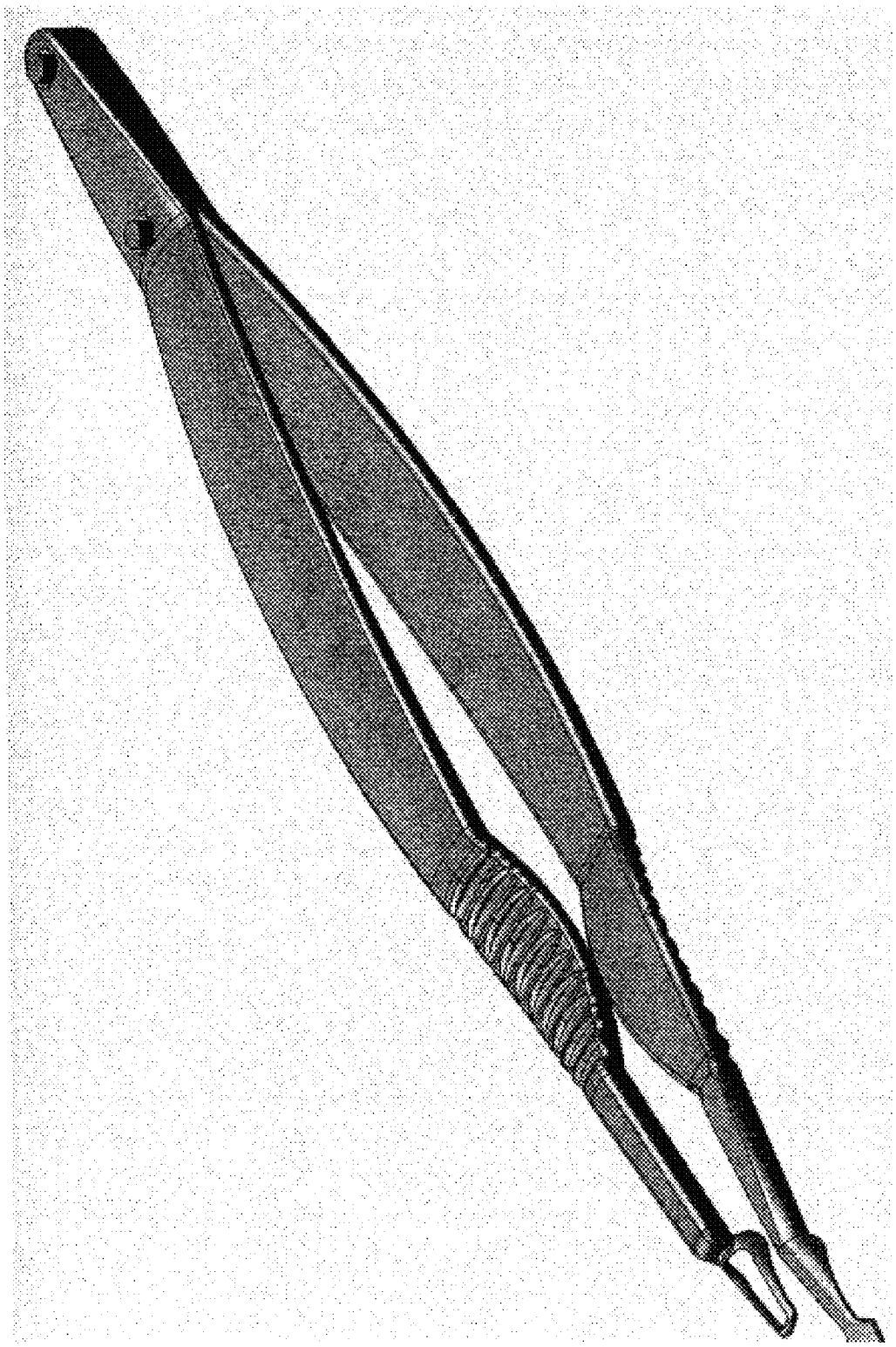
FIG. 18 illustrates a forceps or implant delivery tweezer. Note that a lenticule guide on the lower element extends beyond the upper element. The tip of the guide extends beyond the limit of the lenticule once it is positioned in the device and it is conformed to have a decreased arc chord diameter. This tip would be introduced into the stromal pocket to facilitate introduction of the lenticule.
Figure 19:
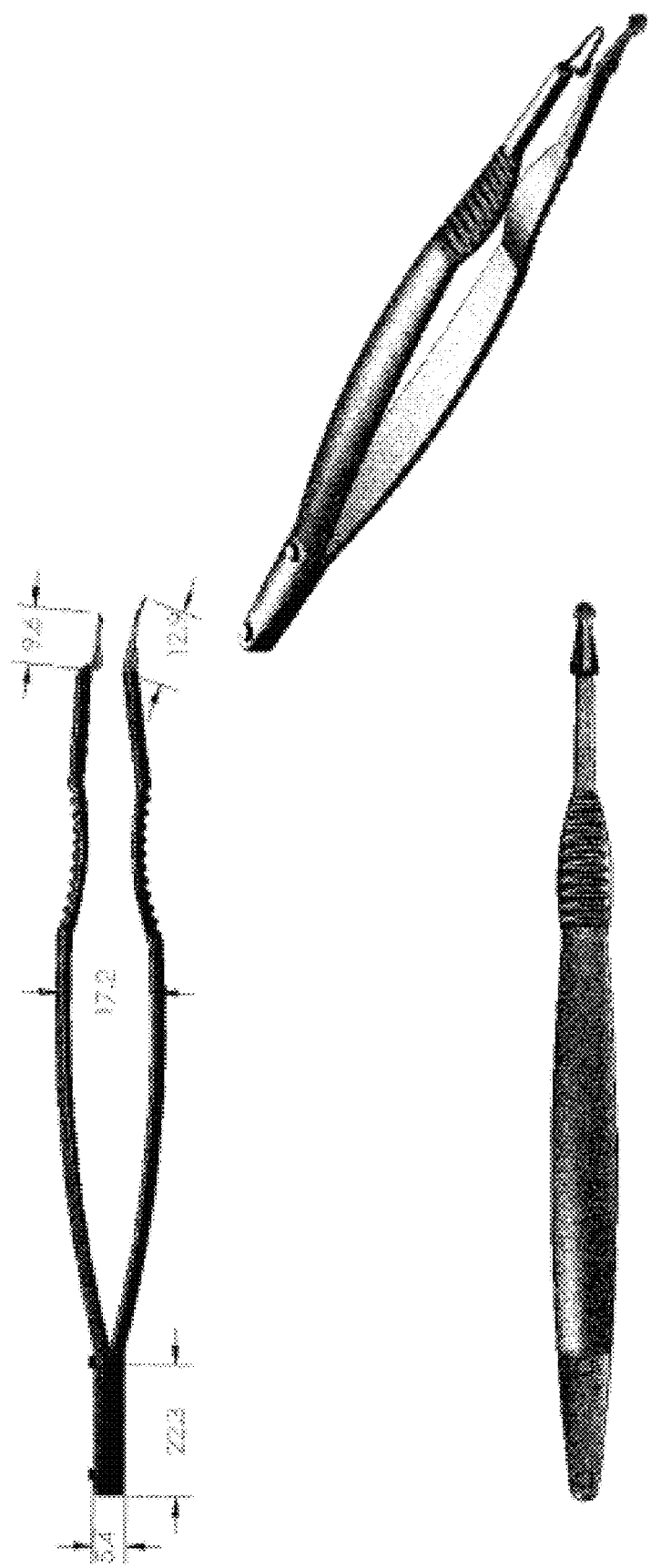
FIG. 19 illustrates a reverse forceps or implant delivery tweezer.
Figure 20:
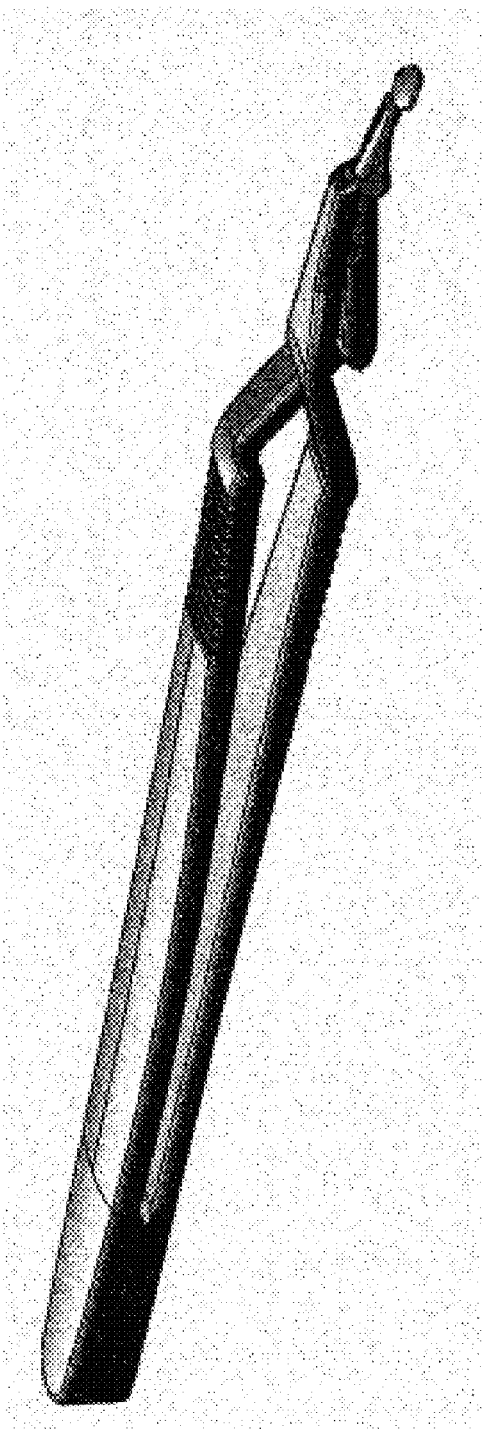
FIG. 20 illustrates a forceps or implant delivery tweezer.
Figure 21:
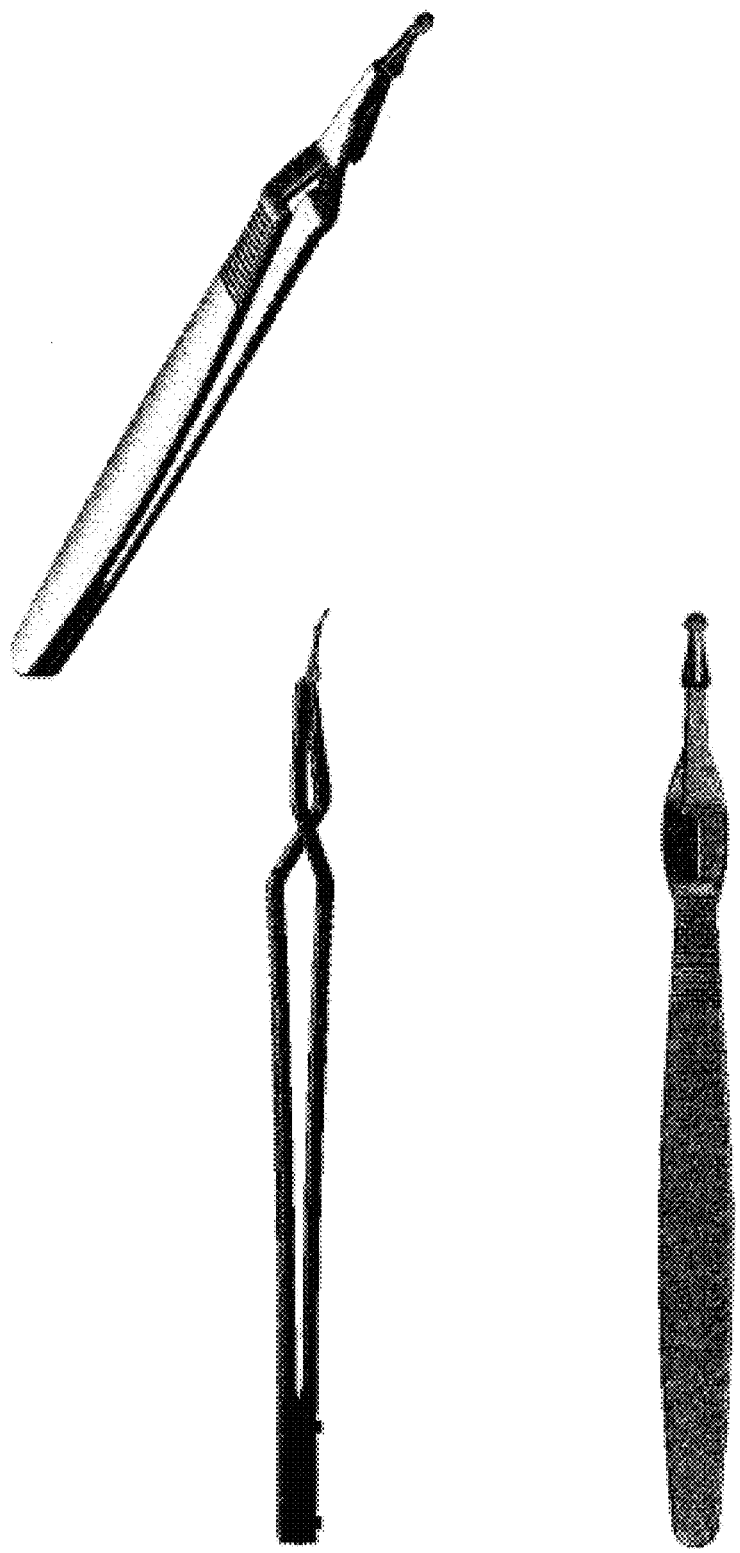
FIG. 21 illustrates a reverse forceps or implant delivery tweezer.
Figure 22:
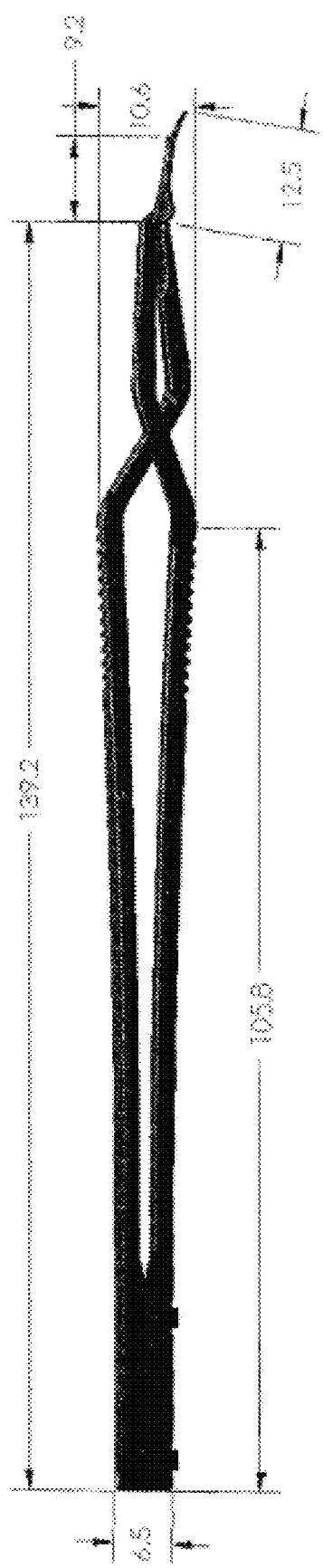
FIG. 22 illustrates a reverse forceps or implant delivery tweezer.
Figure 23:
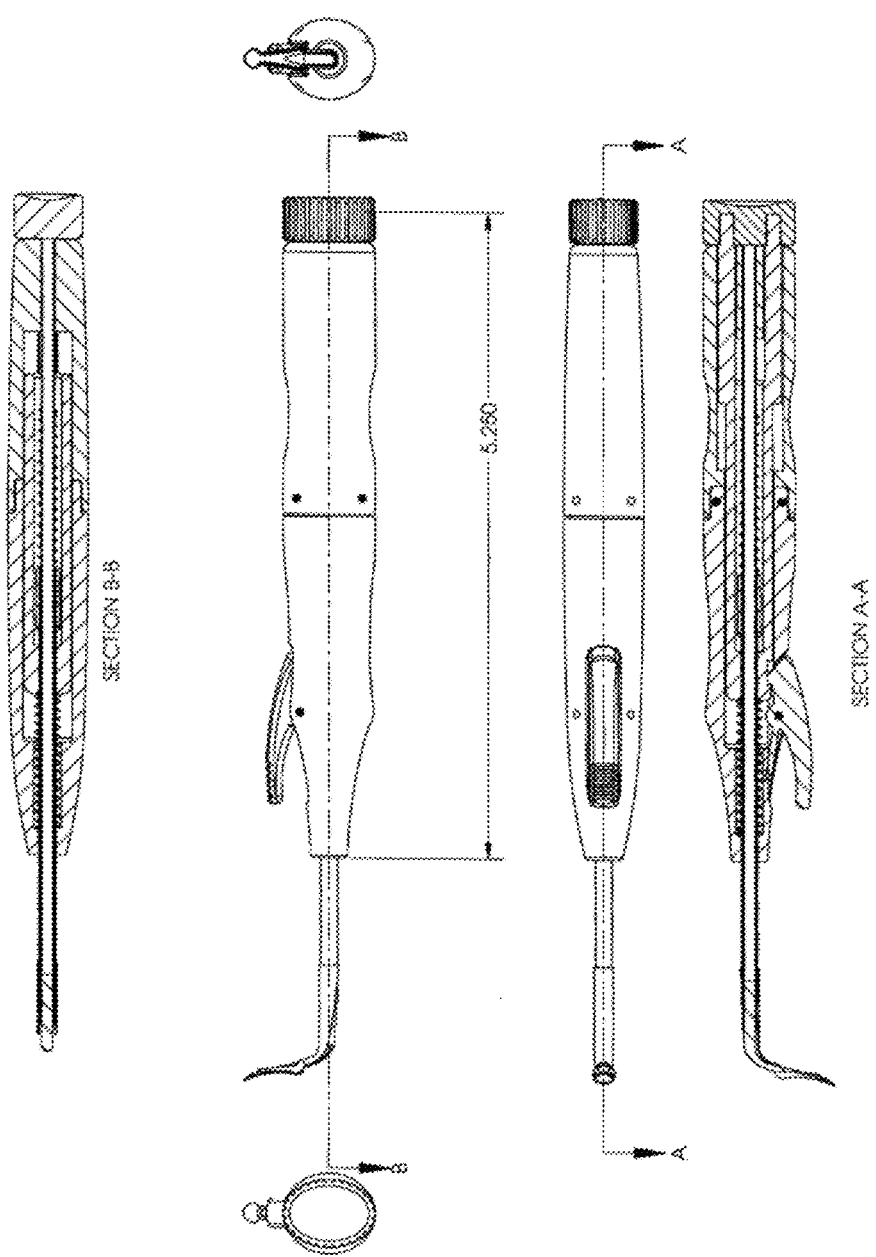
FIG. 23 illustrates another embodiment of a device that alters lenticule curvature to facilitate delivery of a corneal lenticule. In this embodiment the lenticule is deformed by mechanical means with the upper deforming surface being advanced using a "trigger" advance slide mechanism that is integrated into the handpiece.

Further provided are kits comprising cornea replacement lenticules, e.g., shaped as depicted herein and/or one or more, e.g., 2, 3, 4, 5 or more, devices described herein to facilitate the insertion of a deformable object into a surgical site, e.g., a corneal wound bed. In varying embodiments, the kit comprises a cornea replacement lenticule as described and depicted herein, e.g., in FIG. 3, 4 or 5. In varying embodiments, the kit comprises a cornea insertion device as described and depicted herein, e.g., in FIG. 6, 7 or 8. In varying embodiments, the kit comprises an air insufflation needle as described and depicted herein, e.g., in FIG. 16. In varying embodiments, the kit comprises a device that alters the radius of curvature of an object to be implanted into a surgical site as described and depicted herein, e.g., in FIG. 12, 13, 14 or 23. In varying embodiments, the kit comprises a tulip device as described and depicted herein, e.g., in FIG. 12, 13 or 14. In varying embodiments, the kit comprises a guide as described and depicted herein, e.g., in FIG. 9. In varying embodiments, the kit comprises a suction device as described and depicted herein, e.g., in FIG. 10, 11 or 15. In varying embodiments, the kit comprises a forceps or implant delivery tweezer as described and depicted herein, e.g., in FIG. 18 or 20. In varying embodiments, the kit comprises reverse forceps or implant delivery tweezer as described and depicted herein, e.g., in FIG. 19, 21 or 22.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cornea insertion device comprising a handle connected to a guide assembly, the guide assembly comprising:

(i) two prongs that assist in folding a cornea replacement lenticule into a desired shape, wherein the handle comprises a cylindrical hole that serves as a track for the prongs;
(ii) a suction shell positioned under the prongs, the shell comprising a suction line attached to a top portion thereof, allowing for the lenticule to be held in a desired form, positioned in the eye, and then released; and
(iii) a curved guide positioned under the shell, the guide having an arc for folding the lenticule over the top portion for guiding insertion of the lenticule into a recipient bed;

wherein the insertion device conforms a corneal replacement lenticule into a shape of a smaller arc diameter to fit into a cornea recipient bed and places a lenticule skirt into a stromal pocket encircling the recipient bed.

2. The cornea insertion device of claim 1, wherein the curved guide allows folding of the lenticule such that the arc diameter is less than the arc diameter of the superficial aspect of the recipient bed.

3. A kit comprising the cornea insertion device of claim 1.

4. The kit of claim 3, further comprising one or more of:
i) a cornea replacement lenticule;
ii) an air insufflation needle;
iii) an encircling skirt;
iv) a guide for guiding insertion of a lenticule into a recipient bed;
v) a suction device;
vi) a conforming shell;
vii) a forceps; and/or
viii) a reverse forceps.

5. A method of replacing a cornea comprising:
(a) removing native cornea tissue, thereby creating a recipient bed for a replacement cornea;
(b) creating a stromal pocket encircling the recipient bed;
(c) inserting a corneal replacement lenticule into the recipient bed and stromal pocket using a cornea insertion device of claim 1, wherein the lenticule has an arc diameter that exceeds the diameter of the recipient bed, and wherein the insertion device allows folding of the lenticule such that the arc diameter is less than the diameter of the superficial aspect of the recipient bed and facilitates insertion of the corneal lenticule into the stromal pocket encircling the recipient bed.

6. The method of claim 5, wherein after step a) the majority of a recipient's corneal stroma has been removed.

7. The method of claim 5, wherein after step a) only Descemet's membrane and its associated endothelium remains.

8. The method of claim 5, wherein after step a) the entire thickness of a recipient's cornea has been removed.

9. The method of claim 5, wherein the method is performed without sutures.

10. A cornea insertion device comprising a handle connected to a guide assembly, the guide assembly comprising:
(i) two prongs that assist in folding a cornea replacement lenticule into a desired shape, wherein the handle comprises a cylindrical hole that serves as a track for the prongs;
(ii) a suction shell positioned under the prongs, the shell comprising a suction line attached to a top portion thereof, wherein the suction shell is in the shape of an ellipsoid or a tulip having four nodes, allowing for the lenticule to be held in a desired form, positioned in the eye, and then released; and
(iii) a curved guide positioned under the shell, the guide having an arc for folding the lenticule over the top portion for guiding insertion of the lenticule into a recipient bed;

wherein the insertion device conforms a corneal replacement lenticule into a shape of a smaller arc diameter to fit into a cornea recipient bed and places a lenticule skirt into a stromal pocket encircling the recipient bed.

* * * * *